(12) United States Patent
Lepine et al.

(10) Patent No.: US 11,992,572 B2
(45) Date of Patent: May 28, 2024

(54) INDEPENDENT MONITORING CIRCUIT FOR A DISINFECTION SYSTEM

(71) Applicant: GERMITEC, Ivry-sur-Seine (FR)

(72) Inventors: Frédéric Lepine, Saint-Gratien (FR); Cédric Neveu, Montrouge (FR); Clément Deshays, Paris (FR)

(73) Assignee: GERMITEC, Ivry-sur-Seine (FR)

( * ) Notice: Subject to any disclaimer, the term of this patent is extended or adjusted under 35 U.S.C. 154(b) by 446 days.

(21) Appl. No.: 16/801,955

(22) Filed: Feb. 26, 2020

(65) Prior Publication Data

US 2020/0268921 A1    Aug. 27, 2020

Related U.S. Application Data

(60) Provisional application No. 62/810,859, filed on Feb. 26, 2019.

(51) Int. Cl.
*A61L 2/24*    (2006.01)
*A61L 2/10*    (2006.01)

(52) U.S. Cl.
CPC .............. *A61L 2/24* (2013.01); *A61L 2/10* (2013.01); *A61L 2202/11* (2013.01); *A61L 2202/122* (2013.01); *A61L 2202/14* (2013.01)

(58) Field of Classification Search
CPC .......... A61L 2/24; A61L 2/10; A61L 2202/11; A61L 2202/122; A61L 2202/14; A61L 2202/24; A61L 2/28; A61L 2/08
See application file for complete search history.

(56) References Cited

U.S. PATENT DOCUMENTS

| | | | | |
|---|---|---|---|---|
| 6,586,172 B1 * | 7/2003 | Gunn | ..................... | C02F 1/325 |
| | | | | 356/426 |
| 11,385,623 B2 * | 7/2022 | Cella | ..................... | G06N 5/046 |
| 2003/0030011 A1 * | 2/2003 | Brown | ..................... | A61L 2/28 |
| | | | | 422/23 |

(Continued)

FOREIGN PATENT DOCUMENTS

CN    206 687 129    12/2017

OTHER PUBLICATIONS

Extended European Search Report dated Nov. 2, 2020 in European Application No. 20159060.1.

*Primary Examiner* — Regina M Yoo
(74) *Attorney, Agent, or Firm* — B. Aaron Schulman, Esq.; Stites & Harbison, PLLC

(57) ABSTRACT

A system includes a disinfection chamber having an interior volume, a radiation source to emit radiation into the interior volume, a radiation sensor circuit to detect radiation in the interior volume, an independent monitoring circuit to detect radiation in the interior volume, and a computing device that has a memory and a processor. The memory stores first radiation values captured by the radiation sensor circuit, second radiation values captured by the independent monitoring circuit, and computer instructions. The processing unit executes the computer instructions to start the emission of radiation, generate first and second accumulated radiation values from the stored values, respectively, and stop the emission of radiation after reaching a first radiation threshold. Based on a comparison of the first accumulated radiation value to the second accumulated radiation value, a validated disinfection signal or an error signal will be asserted.

13 Claims, 6 Drawing Sheets

(56) References Cited

U.S. PATENT DOCUMENTS

| | | | |
|---|---|---|---|
| 2003/0060747 A1* | 3/2003 | Fries | A61M 1/3681 |
| | | | 210/748.11 |
| 2003/0064001 A1* | 4/2003 | Fries | A61L 2/0011 |
| | | | 250/455.11 |
| 2005/0202395 A1* | 9/2005 | Edrich | A61L 2/10 |
| | | | 604/20 |
| 2014/0341777 A1* | 11/2014 | Deshays | G01K 13/00 |
| | | | 250/354.1 |
| 2015/0144575 A1* | 5/2015 | Hawkins, II | C02F 1/325 |
| | | | 210/748.11 |
| 2016/0279275 A1 | 9/2016 | Deshays et al. | |
| 2020/0179543 A1* | 6/2020 | Deshays | A61L 2/24 |

* cited by examiner

INDEPENDENT MONITORING CIRCUIT FOR A DISINFECTION SYSTEM

CROSS-REFERENCE

This claims the benefit of American Patent Application U.S. 62/810,859 filed Feb. 26, 2019 and hereby incorporated by reference herein.

BACKGROUND

Technical Field

The present disclosure generally relates to an independent monitoring circuit. More particularly, but not exclusively, the present disclosure relates to a disinfection system having a radiation sensor circuit to control a disinfection dose and an independent monitoring circuit to validate the operation of the radiation sensor circuit.

Description of the Related Art

Proper disinfection or sterilization of reusable medical instruments is important in preventing the person-to-person transmission of pathogenic microbes. The level of sterilization and disinfection applied to medical instruments depends on how the device is classified. The Centers for Disease Control (CDC) classifies a medical instrument as a critical item, semi critical item, or noncritical item, depending on the intended use of the device (CDC Guideline for Disinfection and Sterilization in Healthcare Facilities, 2008). In the CDC Guideline, it is stated that critical items confer a high risk for infection if they are contaminated with any microorganism.

Examples of critical items are devices that contact sterile tissue and include surgical instruments, implants, and ultrasound probes used in sterile body cavities. These devices must be sterilized prior to use.

Semi critical items typically contact mucous membranes or non-intact skin. Exemplary semi critical items include such devices as probes used in vaginal, rectal, and urological exams, equipment for respiratory therapy and anesthesia, and certain endoscopes. These medical devices should be free from all microorganisms; however, some small numbers of bacterial spores are considered permissible. Semi critical items require at least high-level disinfection (HLD).

Noncritical items are those that come in contact with non-mucous membranes of intact skin (e.g., blood pressure cuffs and stethoscopes). In contrast to critical and some semi critical items, most noncritical reusable items may be decontaminated where they are used to achieve intermediate or low levels of disinfection and these items typically do not need to be transported to a central processing area for service.

Because critical items confer a high risk for infection when they are contaminated with any microorganism, they are typically subjected to sterilization processes that kill and remove all microorganisms. Similarly, semi-critical items require high-level disinfection (HLD) where population levels of pathogens are reduced to very low levels prior to or between uses. Some common methods for achieving sterilization or high-level disinfection include treatments using steam and/or chemical disinfectants. Chemical treatments are often used where the article to be treated is heat sensitive, and chemical disinfectants suitable for use in sterilizing or disinfecting medical devices include, for example, glutaraldehyde, hydrogen peroxide, ortho-phthalaldehyde, and peracetic acid with hydrogen peroxide. Currently, some common methods for achieving high-level disinfection of semi-critical medical devices include soaking the devices in a chemical bath. The chemical bath method for semi-critical items may include soaking for shorter periods of time than would be required to assure complete sterilization.

Although effective, there are disadvantages to sterilization and disinfection processes that utilize steam or chemical treatments. For example, the high temperature associated with steam sterilization can damage the instrument being sterilized. Additionally, the chemicals used for chemical sterilization or disinfection are often costly to store and dispose of properly, and their toxicity can present risks to personnel handling them. Furthermore, chemical methods and high heat (i.e., severe heating to high temperatures in steam) systems can cause degradation of the materials used to make the medical device being treated. Steam- or chemical-based processes can also be time consuming with some procedures taking between 15-40 minutes to complete, and these procedures typically require the instrument or device to be removed to a central location for treatment and then returned to the clinical setting. Such prolonged process times remove medical devices from service, which may be a serious problem if the device is used in an Emergency Department setting. Factors such as these can lead to non-compliance with the sterilization or disinfection procedures recommended by the Food and Drug Administration.

Some companies provide devices and systems that can achieve high-level disinfection of target articles that are reusable, in a short time, at a low temperature, and done locally within the clinical setting of use.

U.S. Pat. No. 9,364,573, which names at least one common inventor with the present disclosure, and which is assigned to the same assignee as the present disclosure, describes a disinfection method and system using a disinfection chamber with a radiation source, wherein high-level disinfection is achieved within 10 minutes (i.e., 600 seconds or less). The temperature within the disinfection chamber is maintained at a low level. One or both of the ambient temperature within the disinfection chamber and the surface temperature of the target article to be disinfected are monitored so that a threshold temperature, e.g., somewhere between 35° C. to 55° C., will be met and will not be exceeded.

U.S. Provisional Patent Application No. 62/776,974, filed Dec. 7, 2018, which names at least one common inventor with the present disclosure, and which is assigned to the same assignee as the present disclosure, describes methods, devices, and systems that model various portions of disinfection chambers and target articles to assist high-level disinfection for the modeled target articles.

The disclosures of all references mentioned above and throughout the specification, as well as the disclosures of all references mentioned in those references, are hereby incorporated herein by reference.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

Exemplary embodiments of systems, devices, and methods (i.e., the teaching of the present disclosure) describe disinfection systems that include radiation sources to disinfect target objects, radiation sensors to control the disinfection dose of radiation delivered to the target object, and at least one independent sensor that measures a parameter directly linked to the efficacy of disinfection (e.g., the UV dose). In this way, the independent sensor is arranged to validate the proper operation of the radiation sensors that control the disinfection dose, and based on the validation, the disinfection system will either validate or invalidate the disinfection cycle.

A first embodiment may be summarized as a disinfection device, comprising: a disinfection chamber having an interior volume; at least one radiation source configured to emit radiation into the interior volume of the disinfection chamber; a processing unit arranged to execute computer instructions that, when executed by the processing unit, cause the processing unit to direct a delivery of a disinfection dose of the radiation into the interior volume of the disinfection chamber; at least one radiation sensor circuit configured to detect the radiation within the interior volume of the disinfection chamber and further configured, based on how much of the radiation is detected, to determine when said disinfection dose has been delivered; and an independent monitoring circuit arranged to validate a proper operation of the at least one radiation sensor circuit.

In some cases of the first embodiment, the computer instructions comprise further computer instructions that, when executed by the processing unit, cause the processing unit to: direct the at least one radiation source to begin emitting the radiation into the interior volume of the disinfection chamber; generate an accumulated radiation value, the accumulated radiation value representing an amount of radiation detected by the at least one radiation sensor; verify that the accumulated radiation value reaches a first radiation threshold; and direct the at least one radiation source to stop emitting the radiation into the interior volume of the disinfection chamber.

In some cases of the first embodiment, the disinfection device further comprises: a first photodiode arranged in the at least one radiation sensor circuit the first photodiode positioned at a first location in the interior volume of the disinfection chamber; a second photodiode arranged in the at least one radiation sensor circuit the second photodiode positioned at a second location in the interior volume of the disinfection chamber; and a third photodiode arranged in the independent monitoring circuit, the third photodiode positioned at a third location in the interior volume of the disinfection chamber, wherein the first location, the second location, and the third location are different locations. In at least some of these cases, the second location and the third location are in close proximity to each other.

In some cases of the first embodiment, the processing unit is arranged to receive first radiation information from the at least one radiation sensor circuit and arranged to not receive second radiation information from the independent monitoring circuit. In these and other cases, the disinfection device further includes a second processing unit arranged to receive first radiation information from the independent monitoring circuit and arranged to not receive second radiation information from the at least one radiation sensor circuit. In some cases, the at least one radiation sensor circuit and the independent monitoring circuit communicate radiation information to different processing units.

In still some other cases of the first embodiment, the processing unit is communicatively coupled to both the at least one radiation sensor circuit and the independent monitoring circuit. And in some of these cases, the disinfection device further comprises a second processing unit communicatively coupled to only one of the at least one radiation sensor circuit and the independent monitoring circuit. In these or still other cases, the disinfection device further comprises a power supply circuit electrically coupled to only one of the at least one radiation sensor circuit and the independent monitoring circuit.

A second embodiment may be summarized as a disinfection method that comprises: delivering, via at least one radiation source, a disinfection dose of radiation into an interior volume of a disinfection chamber; detecting, via at least one radiation sensor circuit, the radiation within the interior volume of the disinfection chamber; determining, based on how much of the radiation is detected, when said disinfection dose has been delivered; and validating, via an independent monitoring circuit, a proper operation of the at least one radiation sensor circuit.

In some cases of the second embodiment, the method further comprises: directing the at least one radiation source to begin emitting the radiation into the interior volume of the disinfection chamber; generating an accumulated radiation value that represents an amount of the radiation detected by the at least one radiation sensor; verifying that the accumulated radiation value has reached a first radiation threshold; and based on the verifying, directing the at least one radiation source to stop emitting the radiation into the interior volume of the disinfection chamber. And in some cases, the method further comprises: independently executing a first instance of a radiation accumulation algorithm and a second instance of the radiation accumulation algorithm, wherein the first instance of the radiation accumulation algorithm is executed using first radiation information captured by the at least one radiation sensor circuit, and wherein the second instance of the radiation accumulation algorithm is executed using second radiation information captured by the independent monitoring circuit.

In some cases of the second amendment, the first instance of the radiation accumulation algorithm is executed via a first processing unit and the second instance of the radiation accumulation algorithm is executed via a second processing unit, wherein the first and second processing units are different processing units. And in some of these and other cases, determining how much of the radiation is detected includes applying a calibration factor to radiation information received by at least one photodiode of the at least one radiation sensor circuit.

A third embodiment of the present disclosure may be summarized as a system that includes: a disinfection chamber having an interior volume; a radiation source arranged to emit radiation into the interior volume of the disinfection chamber; a radiation sensor circuit arranged to detect the radiation within the interior volume of the disinfection chamber; an independent monitoring circuit arranged to detect the radiation within the interior volume of the disinfection chamber; and a computing device that includes: a memory arranged to store: first radiation values captured by the radiation sensor circuit; second radiation values captured by the independent monitoring circuit; and computer instructions; and; a processing unit arranged to execute the computer instructions which, when executed by the processing unit, cause the processing unit to: direct the radiation source to start emitting the radiation into the interior volume of the disinfection chamber; generate a first accumulated radiation value based on the first radiation values stored in the memory; generate a second accumulated radiation value based on the second radiation values stored in the memory; direct the radiation source to stop emitting the radiation into the interior volume of the disinfection chamber after the first accumulated radiation value has reached a first radiation threshold; determine a validation result based on a comparison of the first accumulated radiation value to the second accumulated radiation value; and assert, based on the validation result, at least one of a validated disinfection signal and an error signal.

In some cases of the third embodiment, the system also comprises: a first photodiode arranged in the radiation sensor circuit; a second photodiode in the radiation sensor circuit; and a third photodiode in the independent monitoring circuit. Sometimes, in these and other cases, the processing unit is arranged to execute the computer instructions which, when executed by the processing unit, cause the processing unit further to: generate the first accumulated radiation value from a mathematical combination of first radiation information captured by at least the first and second photodiodes; and generate the second accumulated radiation value from second radiation information captured by the third photodiode. And in at least some of these cases, the processing unit is arranged to execute the computer instructions which, when executed by the processing unit, cause the processing unit further to: apply at least one first calibration factor during the generation of the first accumulated radiation value; and apply at least one second calibration factor during the generation of the second accumulated radiation value.

In some cases of the third embodiment, the processing unit includes at least two different processors, the at least two different processors including a first processor arranged to receive first radiation information from the radiation sensor circuit and a second processor arranged to receive second radiation information from the independent monitoring circuit.

This Brief Summary has been provided to introduce certain concepts in a simplified form that are further described in detail below in the Detailed Description. Except where otherwise expressly stated, the Brief Summary does not identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1:
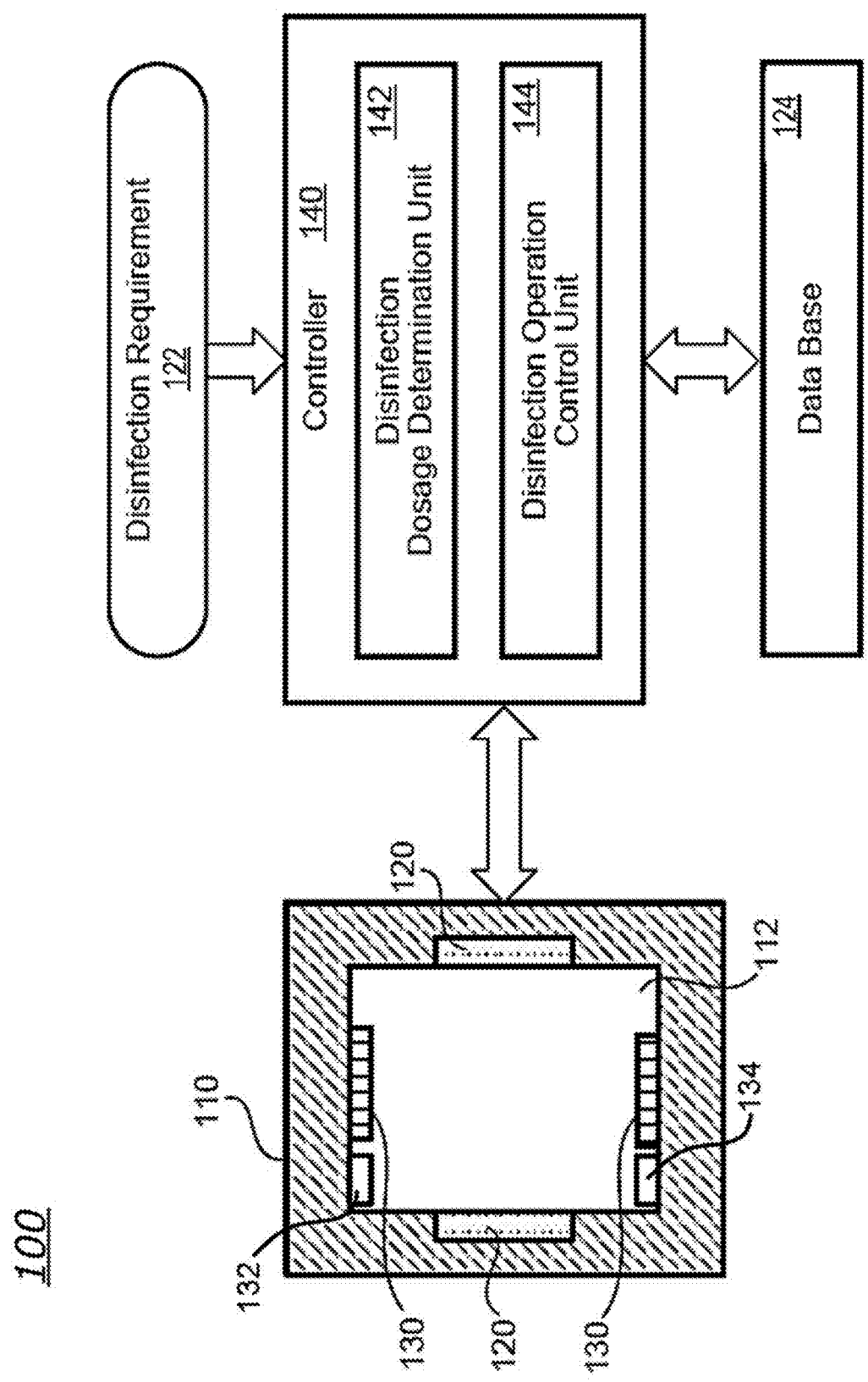
FIG. 1 depicts an exemplary disinfection device embodiment.

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

An embodiment of the present invention includes a disinfection chamber having an interior volume. One or more radiation sources are arranged to emit radiation into the interior volume of the disinfection chamber when so directed by a processor-based system. One or more radiation sensor circuits are arranged to detect the radiation that is emitted into the interior volume of the disinfection chamber. The radiation sensor circuits may be calibrated to detect, capture, accumulate, or otherwise measure how much radiation is reaching a "cold spot" of an object placed in the disinfection chamber.

In at least one exemplary case, a cold spot on the object placed in the disinfection chamber is determined. Such a cold spot, for at least the purposes of the example, is a location on the object that will receive a "least" amount of radiation during a disinfection cycle.

In addition to the radiation sensor circuits, the system also includes an independent monitoring circuit arranged to detect the radiation within the interior volume of the disinfection chamber; and a computing device. The computing device includes a memory, a processor, and other operative circuits that carry out the functions of the disinfection chamber. The memory is arranged to store first radiation values captured by the radiation sensor circuit and second radiation values captured by the independent monitoring circuit. The memory is also arranged to store the computer instructions that are executed by the processing unit.

When the processing unit executes the computer instructions, the radiation source will be directed to start emitting radiation into the interior volume of the disinfection chamber. A first accumulated radiation value will be generated based on the first radiation values stored in the memory, and a second accumulated radiation value will be generated based on the second radiation values stored in the memory. When the first accumulated radiation value has reached a first radiation threshold, the radiation source will be directed to stop emitting the radiation into the disinfection chamber. A validation result will be determined based on a comparison of the first accumulated radiation value to the second accumulated radiation value, and based on the validation result, a validated disinfection signal or an error signal will be asserted.

Exemplary embodiments of systems, devices, and methods (i.e., the teaching of the present disclosure) describe disinfection systems that include radiation sources to disinfect target objects, radiation sensors to control the disinfection dose of radiation delivered to the target object, and at least one independent sensor that measures a parameter directly linked to the efficacy of disinfection (e.g., the disinfection dose). In this way, the independent sensor is arranged to validate the proper operation of the radiation sensors that control the disinfection dose, and based on the validation, the disinfection cycle can be either validated or invalidated as the case may be.

It is noted that the inventive concepts discussed in the present disclosure are clearly different from the concepts taught in other disinfection systems, and particularly those that employ a chemical bath disinfection means. In these competitive systems, an impregnated paper product is placed in the chemical bath, and the paper product changes color in accordance with a pH level. In such systems, the main sensor (i.e., the pH-testing paper) does not measure parameters that are directly linked to the efficacy of disinfection. Instead, such systems only validate that the conditions for the chemical bath disinfection are satisfactory right at the point where the paper is located. Any or all of the other parts of the liquid bath may be unsatisfactory, and the sensor (i.e., the pH-testing paper) of the chemical bath is unable to perform this detection.

FIG. 1 shows a disinfection system 100 in an exemplary operating environment. Disinfection system 100 includes a disinfection chamber 110 having an interior volume 112. One or more radiation sources 120 are coupled to the interior volume 112, and these radiation sources 120 are directed by a processing unit such as controller 140 to emit radiation light rays into interior volume 112 when in operation. One or more radiation sensor circuits 130 are physically, communicatively, electronically, or otherwise coupled within interior volume 112 and arranged to detect radiation within interior volume 112. One or more non-radiation detection sensor circuits 132 are physically, communicatively, electronically, or otherwise coupled within interior volume 112 and arranged to detect non-radiation parameters such as intensity, time, volume, and the like within interior volume 112. Also arranged within the interior volume is at least one independent monitoring circuit 134. The independent monitoring circuit 134 is arranged to validate the proper operation of the at least one radiation sensor circuit 130.

The one or more sensor circuits 130, 132, and monitoring circuits 134, may be arranged in a manner specifically for a certain type of target article 240 (FIG. 2B) to be disinfected in disinfection chamber 110. For example, sensor circuits 130 may be arranged in a manner suitable for detecting radiation intensity information on the surface portions of a target article 240.

In the present disclosure, sensor circuits arranged to detect disinfection radiation are referred to herein as sensor circuits 130, and sensor circuits that are arranged to validate the operation of the sensor circuits 130 are referred to herein as independent monitoring circuits 134. In at least some cases, the independent monitoring circuits 134 are also arranged to detect disinfection radiation. In contrast, sensor circuits arranged to detect other non-disinfection-radiation phenomena, such as temperature, time, vibration, weight, humidity, liquid, continuity, and the like, are referred to herein as sensor circuits 132. Accordingly, in addition to one or more sensor circuits 130 (e.g., photodiodes) and one or more independent monitoring circuits 134 capable of detecting or quantifying the disinfecting intensity delivered within the interior volume 112 and to the target article 240 to be disinfected, the disinfection chamber 110 may also include one or more temperature sensor circuits, one or more foreign object detection sensor circuits (e.g., infrared emitters and detectors, cameras, accelerometers, load cells, or the like), one or more "door open" sensor circuits (e.g., normally-open or normally closed switches, light detectors, continuity circuits, or the like), or any other types of non-disinfection-radiation sensor circuits. These other, non-disinfection-radiation sensor circuits may each, individually or collectively, be referred to as sensor circuits 132.

One or more of disinfection chambers 110, radiation sources 120, sensor circuits 130, 132, and independent monitoring circuits 134, are communicatively coupled to a controller 140. Controller 140 includes a disinfection exposure determination unit 142 and a disinfection operation control unit 144 arranged to execute a generated disinfection program. Besides the data exchange with disinfection chamber 110, radiation sources 120, sensor circuits 130, 132, and monitoring circuits 134, controller 140 may also communicate with one or more databases 124 and/or disinfection requirement inputs 122 in achieving its functions and operations.

FIGS. 2A-2E are exemplary disinfection chambers, each of which may be referred to as an exemplary disinfection system 100. FIGS. 2A-2E may be referred to collectively as FIG. 2. In the individual figures, components retain the same reference number, and in some cases, to avoid obscuring certain features, some of the reference numbers are shown in one figure, while the same reference numbers are not shown in other figures even when the particular component is present.

In FIG. 2, disinfection system 100 is a high-level disinfection device that includes a disinfection chamber 110 having an interior volume 112 and one or more radiation sources 120 configured to emit radiation into the interior volume 112 of the disinfection chamber 110. At least some of the radiation sources 120 represented in FIG. 2 are optional. In FIG. 2B, for example, two optional radiation sources 120 at the bottom of the interior volume 112 are shown in dashed lines. In some cases, the two radiation sources 120 at the bottom of the interior volume 112 are included, in some cases, other radiation sources 120 are optionally included or omitted.

Figure 2B:
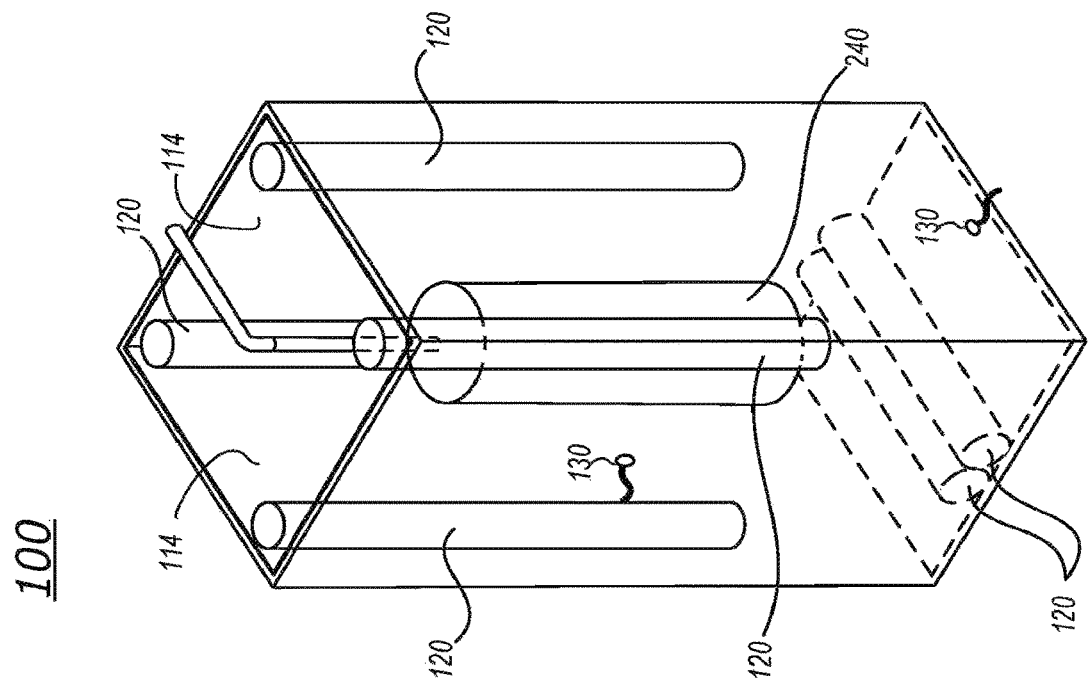
FIGS. 2A-2E show exemplary disinfection chambers, each of which may be referred to as an example system.
Figure 2A:
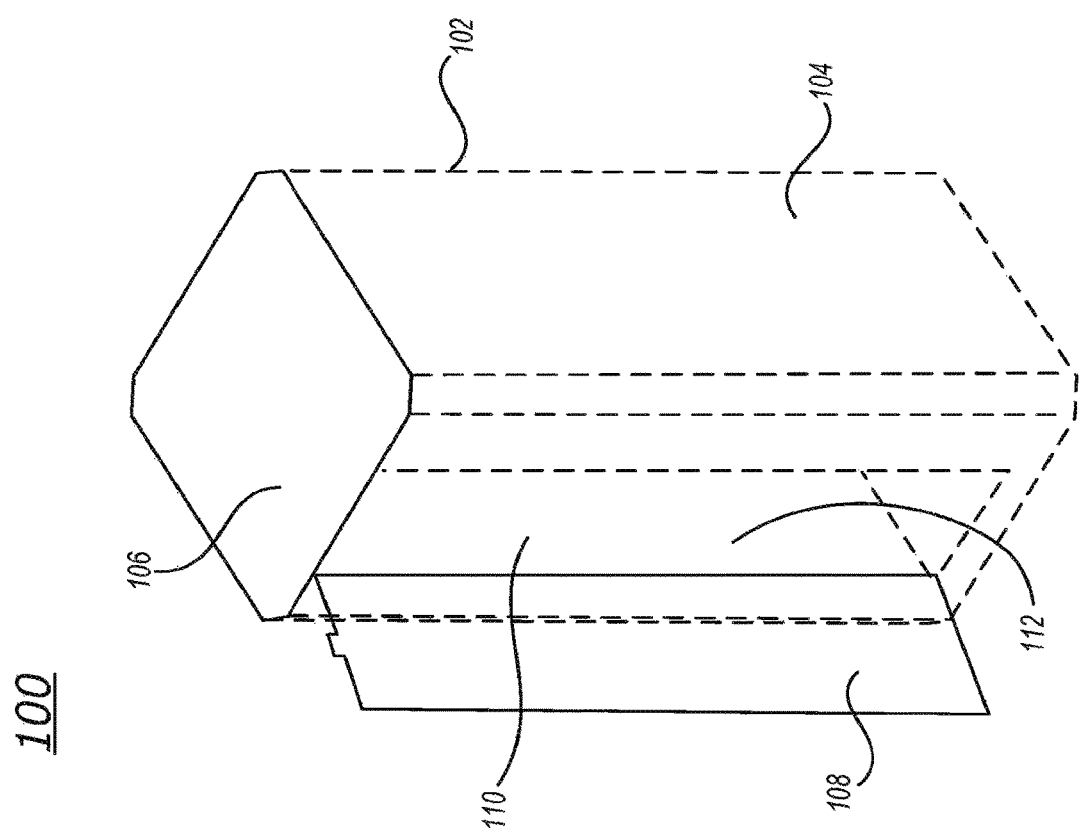

Disinfection chamber 110 includes a housing 102 having a plurality of sidewalls 104, a top 106, and a door 108 disposed within one of the sidewalls 104 for accessing the interior volume 112. Although the door 108 in FIG. 2A is shown as being rotatably movable about a vertical axis, other door configurations may be used, which will also provide adequate access to the interior volume 112. It is understood that upon opening door 108, an access opening is created in the disinfection chamber sidewall 104, and the access opening communicates with the interior volume 112. Other arrangements of disinfection chambers are of course contemplated.

The interior volume 112 of the disinfection chamber 110 may include one or more reflective surfaces 114 arranged to facilitate reflections of radiation light rays emitted from radiation sources 120 such that a rapid and low temperature disinfection is achieved. The reflective surface 114 is typically formed from one or more materials having at least 30% reflectivity. By "at least 30% reflectivity," it is meant that no more than 70% of the incident UV radiation, particularly in the UV-C range, will be absorbed, and the rest of the incident radiation will be reflected via one or both diffuse and specular reflection. Reflective materials that may be particularly useful in a disinfection chamber include, but are not limited to, aluminum, glass, magnesium, stainless steel, polyvinyl alcohol, polytetrafluoroethylene, substrate materials treated with barium sulfate-containing paints, and alloys, derivatives, and copolymers thereof. In some variations, the reflective surface comprises aluminum, polished to a "Grand Brilliant" condition. In other variations, the reflective surface may be formed using polytetrafluoroethylene PTFE, or PTFE and similar polymers may be coated by various means onto another substrate, to form the reflective surface. In particular embodiments, the reflective interior surfaces of the disinfection chamber are formed to be as reflective as available manufacturing techniques provide. Such an approach facilitates disinfection processes that utilize high intensity disinfection radiation carried out at low temperatures.

The interior surfaces of the interior volume 112 may be positioned and shaped to reduce the absorption of UV radiation by the interior surfaces and instead reflect and redirect the UV radiation within the interior volume 112 of disinfection chamber 110 and onto the one or more target articles 240 positioned within the interior volume 112. The material choice and configuration of the interior volume 112 of disinfection chamber 110 may be selected to promote preferential extinction of certain UV or other wavelengths of electromagnetic energy that can contribute to increased temperatures within the interior volume 112 (i.e., longer wavelengths of radiation). That is, the shape of the interior volume 112 may contribute to the quick and efficient directing of radiation to the target article 240. For example, it may be configured that the radiation passing through the middle of the interior volume 112 of the disinfection chamber 110, where the target article 240 is to be positioned, and the reflective material(s) employed in the interior volume 112 may contribute to the reflection (e.g., re-radiation or re-emission) of radiation with low loss (i.e., approximately the same amount of energy returns from the surface as was incident). In particular embodiments, the interior walls of the interior volume 112 are constructed and configured to provide low loss of UV-C radiation emitted from the one or more UV radiation sources 120 (not specifically shown in FIG. 2A for simplicity purposes). Such embodiments increase the likelihood that radiation (e.g., UV-C radiation) useful for disinfection will be reflected one or more times inside the chamber until the radiation impinges upon the article to be disinfected where it may be absorbed and extinguished, reflected, or re-emitted. In this way, for a given amount of total energy released into the chamber, which also may include some amount of infrared or heat energy, an improved utility is made of the useful radiation band energy (e.g., UV-C radiation band energy) in disinfecting the target article 240 (e.g., medical device or instrument), while reducing the amount of thermal heating of the target article 240.

As set forth in the teaching herein, the disinfecting radiation utilized can be UV-C radiation, and in embodiments that utilize UV-C radiation, the one or more radiation sources 120 may be any commercially available device suitable for emitting sufficient UV-C radiation to carry out high-level disinfection. Where one source 120 of UV-C radiation is coupled to the disinfection chamber 110, that source 120 will emit sufficient UV-C radiation into the interior volume 112 of the disinfection chamber 110 to carry out high-level disinfection as detailed herein. Where two or more sources of UV-C radiation are coupled to the disinfection chamber 110, the UV-C radiation sources 120 may each be capable of emitting sufficient UV-C radiation to carry out high-level disinfection. Alternatively, in embodiments of the system 100 including two or more UV-C sources 120 coupled to interior volume 112 of disinfection chamber 110, such radiation sources 120 may each, on their own, emit insufficient UV-C radiation to achieve high-level disinfection, but when the individual outputs of UV-C radiation emitted from the two or more sources 120 are combined, the total output of UV-C radiation is sufficient to achieve high-level disinfection.

Each radiation source 120 may be coupled to interior volume 112 through various approaches. For example, radiation source 120 may be locally attached to interior volume 112 to emit UV-C radiation rays into interior volume 112, as shown in FIG. 2B for illustrative purposes. In further examples, a radiation source 120 may be remotely coupled to interior volume 112. For example, radiation source 120 may be a standard laser, or solid state laser photodiode, and may be employed as a source of disinfecting energy for a stand-alone disinfection chamber 110, along with appropriate optical conductors and couplers to emit UV-C radiation rays into interior volume 112. Further, in some embodiments, a direct or conducted source of UV radiation could be steered, via a mirror or other device, or scanned along a target article 240 positioned within interior volume 112. In other embodiments, disinfection chamber 110 may include a movable attachment assembly, which is not specifically shown to avoid unnecessarily cluttering the figure, within interior volume 112 such that a target article 240 may be positioned on the movable base and may be moved past a stationary radiation emission region. A processing unit of controller 140 (FIG. 1) may control the radiation source 120 and the movable base to rotate or move in opposite directions to provide preferential exposure of the target article 240 to the UV radiation.

Though the devices, methods, and systems provided herein are primarily described with reference to UV-C radiation as the disinfecting radiation within the disinfection chamber, this is for illustrative purposes only. The radiation or energy used in the disinfection system 100 may also be or include UV-A radiation, UV-B radiation, or even non-UV radiation, alone or in various combinations. It is to be further understood that, within the interior volume 112, exposure of the articles to UV radiation may be carried out in a variety of ways.

Instead of UV radiation, such as UV-C radiation, some variations of the devices described herein may use a flash source of energy. A flash source of energy emits extremely high intensity disinfecting radiation. The flash source of energy can provide high-level disinfection of one or more contaminated articles in an acceptably short period of time. In certain embodiments, a flash source of energy may deliver disinfecting radiation to the one or more articles at such a high rate that high-level disinfection is achieved in period of time selected from 10 seconds or less, 5 seconds or less, 3 seconds or less, and 2 seconds or less. A flash source of energy as contemplated herein may be selected to deliver any selected disinfecting radiation. For instance, a disinfection system as described herein may include a flash source of energy that emits electron beam, gamma-ray, x-ray, gas-plasma, or UV-C radiation. The biologically active mechanism of disinfection of the flash source may be different for the different sources. For example gamma-ray may fully kill a pathogen, whereas UV-C may leave the pathogen alive but biologically sterile and unable to reproduce.

Where a flash source of energy is used, one radiation source 120 of disinfecting radiation may be all that is needed in the interior volume 112 of disinfection chamber 110. In such embodiments, to achieve generally homogenous or uniform radiation exposure on the target article 240, the radiation emitted by the flash source may first strike a surface that will spread and distribute the radiation before hitting the target. In this case, the target will receive primarily indirect rather than direct, illumination. In other words, the disinfection device could be configured so that the source or sources, of any appropriate type, are located in a different part of the device than the target. Since the energy spectrum emitted by some types of flash sources may be broad, it may be helpful to interpose a filter between the source and the target so only the spectrum of interest is allowed to pass to the disinfection chamber. The filter may serve to minimize the presence within the chamber of infrared energy, which does not disinfect but will otherwise heat the chamber and thus raise its temperature and that of objects contained therein. Said filters may also be useful when implemented with the other radiation sources mentioned herein. Combinations of disinfection energy sources may be used in the devices and systems described herein. Where two or more different disinfection energy sources are used, they may be applied sequentially, in parallel, or in various combinations and orders. The inclusion and use of two or more different sources of disinfecting energy may prove advantageous in situations where certain pathogens are more susceptible to a particular source of disinfection energy, and in order to reduce overall exposure of the target article 240, it may be useful to employ a variety of radiations sources, durations, and doses to achieve acceptable disinfection for pathogens of interest.

Where the devices and systems described herein utilize UV radiation, such as UV-C radiation, the one or more UV radiation sources 120, the one or more UV radiation sensor circuits 130, and/or the one or more independent monitoring circuits 134 are positioned within the interior volume 112 of disinfection chamber 110 in a manner that facilitates and validates rapid, low temperature disinfection. In general, the configuration of the disinfection chamber, the sources of disinfecting radiation, and the sensors detecting disinfecting radiation will be selected to provide and confirm a selected exposure of the one or more articles to radiation and/or optimize transmission of radiation from the one or more sources to efficiently and reproducibly target an article.

As described herein, a disinfection chamber 110 according to the present teaching may be coupled to a single radiation source 120 of disinfecting radiation, such as one UV-C radiation source. In such embodiments, the radiation source may be positioned on a top or bottom of the chamber. Alternatively, depending on the positioning of the articles to be disinfected, the single radiation source 120 may be positioned on a side of the disinfection chamber or, where the disinfection chamber includes multiple sides, at an intersection formed at an intersection of two sides. However, the devices and systems described herein are not limited to disinfection chambers having a single source of disinfecting radiation.

The disinfection chamber 110 included in the devices and systems 100 according to the present description may utilize multiple radiation sources 120, of the same or different variety, and different embodiments of a disinfection chamber 100 having multiple sources 120 of disinfecting radiation are detailed herein and illustrated in the accompanying figures. Such embodiments may be advantageous where the surface of the one or more target articles 240 to be disinfected are more complex than a single flat surface. For example, a target article 240 to be disinfected, such as an endotracheal probe or an ultrasound probe, may have two or more of a front, back, lateral, and dorsal and/or ventral surface that require disinfection. In such a scenario, it may be difficult to deliver high intensity radiation to each surface of target article 240 with a single source or type of disinfecting radiation. Accordingly, in some embodiments of the disinfection devices 100 described herein, the radiation sources 120, and other structures are arranged to disinfect one particular type of target. That is, the sources 120 and/or other structures may provide illumination to each surface of the specific target, but the device would not function effectively if a different type of target was placed in the disinfection chamber.

Radiation sources 120 that may be employed in devices and systems as described herein are available in the art, and include, for example, UV-C emitting lamps. UV-C emitting lamps, also referred to herein as "tubes," are available commercially from various sources, including Philips Lighting B.V., and can be obtained in different shapes, sizes, input energy, and UV-C output ratings. Suitable UV-C tubes for use as a UV-C energy source include low-pressure mercury vapor discharge lamps. However, the disinfection chambers are not limited to a particular UV-C source. Any source capable of emitting UV-C light within the selected UV-C wavelength at an output rating that contributes to the disinfection of a target article 240 could be used in the devices disclosed herein. For example, in addition to or as an alternative to one or more UV-C tubes, one or more lasers or photodiodes, or arrays of sources, or combinations of types of sources designed to emit UV-C light may be used to deliver disinfecting radiation within the disinfecting chamber.

In particular embodiments, the one or more sources of UV-C radiation included in the disinfection chambers 110 described herein provide a total UV-C output within the interior volume 112 of the disinfection chamber 110 that is selected to be at least 5 Watts of radiant power. Selection of such a radiation source, which can deliver a high-power dose of radiation, may be preferred to shorten a disinfection cycle. That is, by selecting a high-power radiation source, the energy is delivered rapidly, which may reduce the duration of radiation exposure and also reduce the amount of heat generated by the radiation. In other cases, the one or more radiation sources 120 may be selected to provide a total UV-C output within the chamber's interior volume 112 selected from at least 10 W, at least 15 W, at least 20 W, at least 25 W, at least 30 W, at least 40 W, at least 50 W, at least 75 W, at least 90 W, and at least 100 W of radiant power. Where UV-C sources are used as the one or more sources 120 of disinfecting radiation, the frequency band of UV-C light emitted from the one or more sources may be selected from between about 240 nm and about 270 nm and between about 255 nm and about 265 nm.

Figure 2C:
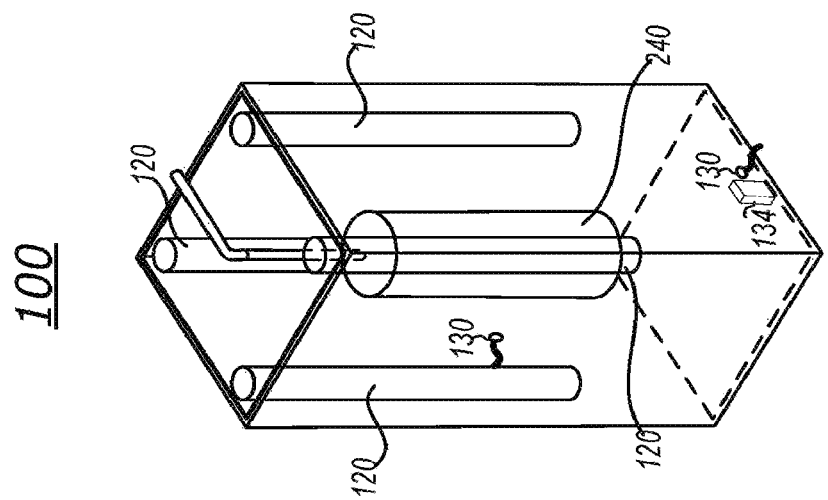
Figure 2D:
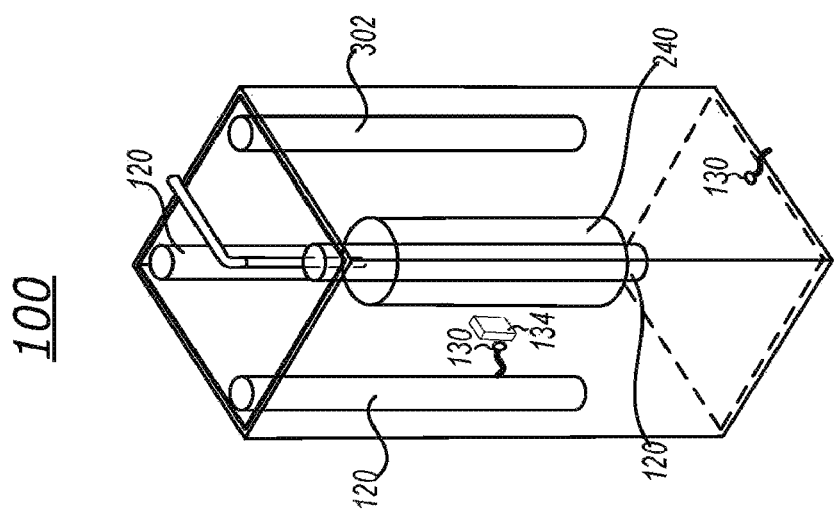
Figure 2E:
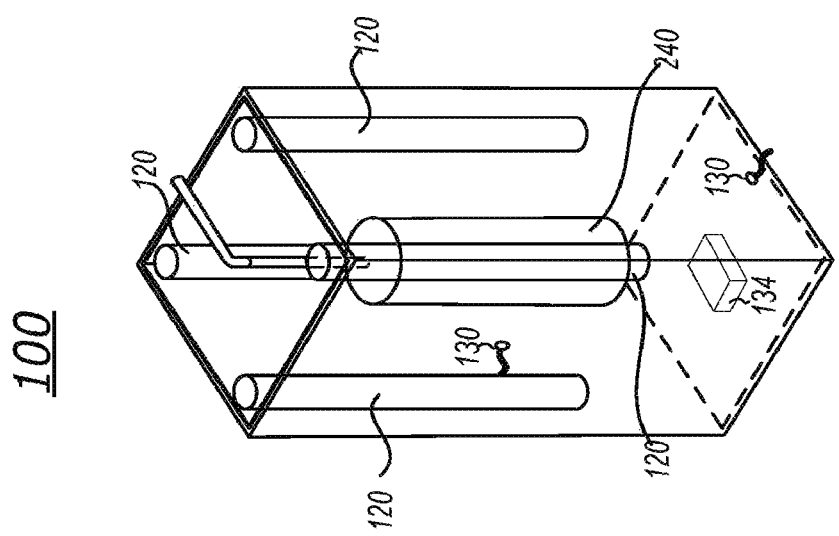

FIGS. 2C, 2D, and 2E are additional exemplary disinfection chambers. In the embodiments, a processing unit of the controller 140 (FIG. 1) is arranged to execute computer instructions that, when executed by the processing unit, cause the processing unit to direct a delivery of a disinfection dose of the radiation into the interior volume 112 of the disinfection chamber 110. Each of the embodiments in FIGS. 2C-2E includes two radiation sensor circuits 130 configured to detect the radiation within the interior volume 112 of the disinfection chamber 110. The radiation sensor circuits 130 are further configured, based on how much of the radiation is detected, to determine when said disinfection dose has been delivered. That is, in some cases, the processing unit of controller 140 executes computer instructions that cause the processing unit to direct at least one radiation source 130 to begin emitting the radiation into the interior volume 112 of the disinfection chamber 110. The radiation sensor circuits 130 work cooperatively with the controller 140 to accumulate radiation samples, mathematically combine (e.g., generate an accumulated radiation value via an average or in some other way) the accumulated samples, apply one or more calibration factors, scaling factors, or other factors, and determine whether or not the disinfection dose of radiation has been achieved. In these cases, the accumulated radiation value at one or more radiation sensor circuits represents an amount of radiation detected by the at least one radiation sensor circuit, and a comparison if performed to verify that the accumulated radiation value, which may be representative of a single radiation sensor circuit or a collection of radiation sensor circuits, reaches a first radiation threshold. If the radiation threshold is reached, the processing unit of the controller 140 will direct the at least one radiation source 120 to stop emitting the radiation into the interior volume 112 of the disinfection chamber 110.

In at least some cases, the independent monitoring circuit 134 is arranged along the lines of the radiation sensor circuits 130. The independent monitoring circuits 134 and radiation sensor circuits 130 are formed along the same lines, but data from the two different types of circuits is processed differently. For example, in an exemplary embodiment, a disinfection chamber 100 is arranged with two radiation sensor circuits 130 and one independent monitoring circuit 134. Each of the circuits may include a photodiode circuit which may include operative voltage divider circuitry, power supply circuitry, analog-to-digital conversion circuitry, and other such circuitry. Hence, for the sake of the embodiment, a first photodiode is arranged in the at least one radiation sensor circuit 130 and positioned at a first location in the interior volume of the disinfection chamber, a second photodiode is arranged in the at least one radiation sensor circuit 130 and positioned at a second location in the interior volume of the disinfection chamber, and a third photodiode is arranged in the independent monitoring circuit 134 and positioned at a third location in the interior volume of the disinfection chamber.

The first location, the second location, and the third location are different locations. In FIG. 2C, the first location, the second location, and the third location are also separated by one or more inches and arranged in different orientations. Accordingly, each photodiode circuit may receive and accumulate a different amount of radiation. The difference in received radiation may be proportionally determined, calculated, or otherwise known. In this way, it is possible to determine how much accumulated radiation is received at each photodiode, and using these accumulated values, it can be determined within a selected validation threshold if the other photodiodes received the "proper" or otherwise correct amount of radiation.

In FIG. 2C, the first location of the first radiation sensor circuit 130 (e.g., photodiode), the second location of the second radiation sensor circuit 130 (e.g., photodiode), and the third location of the independent monitoring circuit 134 are separated and not in close proximity. In FIG. 2D, the first location of the first radiation sensor circuit (e.g., photodiode) and the third location of the independent monitoring circuit 134 are in close proximity. And in FIG. 2E, the second location of the second radiation sensor circuit 130 (e.g., photodiode) and the third location of the independent monitoring circuit 134 are in close proximity.

Despite the close or distant proximity, the monitoring sensor 134 is arranged to operate independently from the radiation sensor circuits 130. In some cases, the processing unit of controller 140 (FIG. 1) is arranged to receive first radiation information from at least one of the radiation sensor circuits 130 and arranged to not receive second radiation information from the independent monitoring circuit 134. In this case, for example, a second independent processing unit may be arranged to receive radiation information from the independent monitoring circuit 134 and arranged to not receive radiation information from the at least one of the radiation sensor circuits. That is, each of the radiation sensor circuits 130 and independent monitoring circuits 134 communicates its accumulated radiation values to different processing units. In at least one case, information regarding the accumulated radiation values may be communicated to different processing units, various resulting information may be communicated back to a common processing unit. In at least some other additional or alternative cases, the radiation sensor circuits 130 and independent monitoring circuits 134 may have separate and distinct power supplies.

Figure 3:
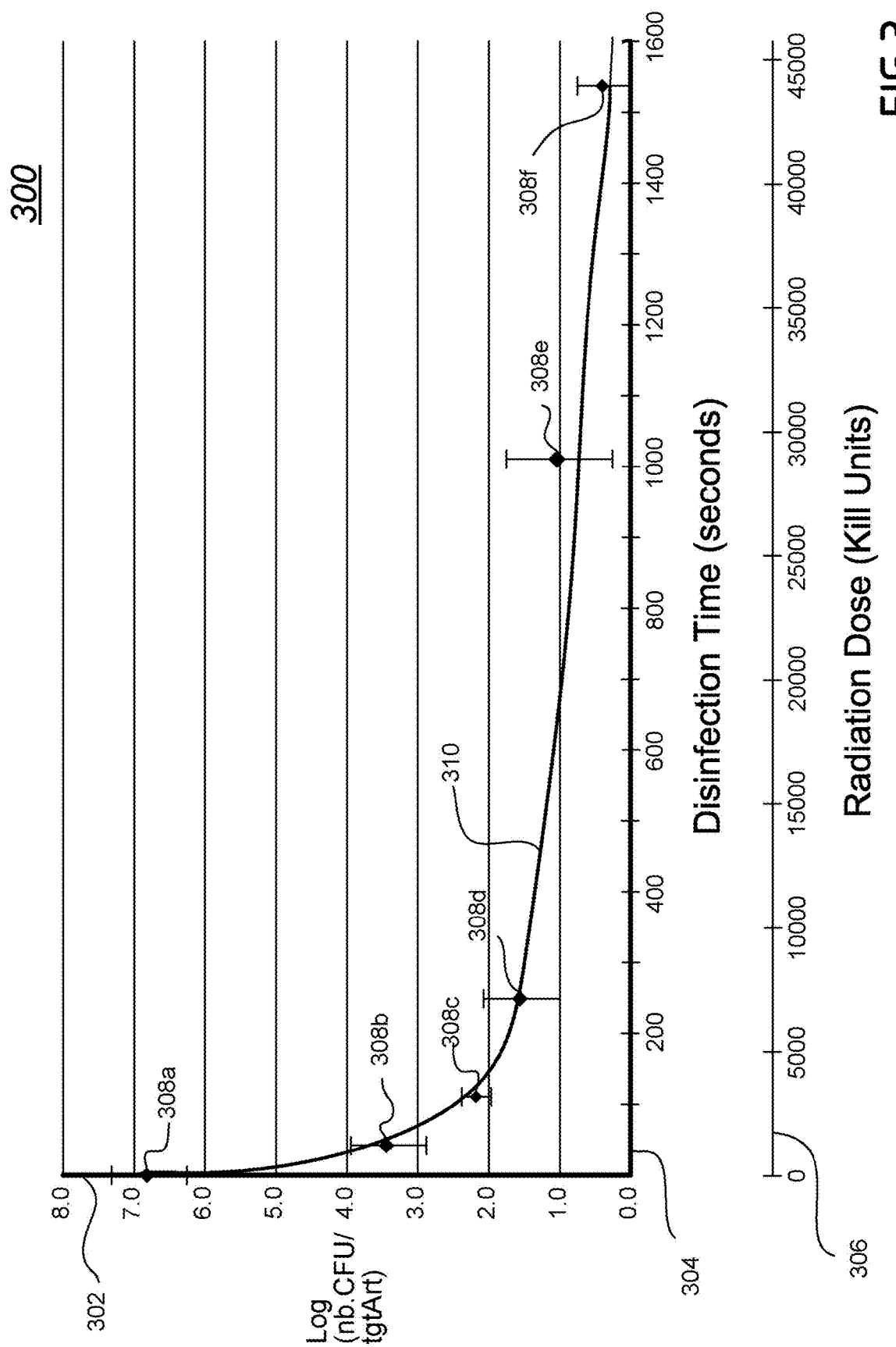
FIG. 3 is an exemplary kill curve.

FIG. 3 is an exemplary kill curve 300. To facilitate the discussion of kill curve 300 of FIG. 3 and the understanding of a target dose of radiation, certain concepts are now explained. One such concept is the principle of proportionality of energy fluence ratios. Energy Fluence Rate may be understood by those of skill in the art as the flow of energy in watts per square meter (Watts/m$^2$), which in the present disclosure is photonic energy in the UV wavelength range, coming from all directions through or across an infinitesimally small sphere of unit area (1) within the interior volume 112 of the disinfection chamber 110. Integrating this energy flow over this surface and over time calculates a "dose" in Joules (J) that has been delivered from the radiation sources 120 and delivered, presumably, at the surface of the target article 240. This energy may be absorbed and extinguished, re-emitted, reflected/scattered, or captured and transported elsewhere. At a given point or elemental surface in the disinfection chamber 110, the dose of energy delivered to the point or surface is the integral (i.e., summation) of the irradiance over the total exposure. Another related term, irradiance, in W/m2, is used, and in a situation where all inbound radiation is coming from a single direction and impinging onto a surface, irradiance and fluence are identical. Fluence takes into account that the radiation may be inbound and reach a surface from many directions, which is the case in the disinfection chamber 110 of the present disclosure due to one or more radiation sources 120 and an interior volume 112 with one or more reflective surfaces. The radiation is broadly distributed as an illuminating field of photonic power with the intention of fully exposing all surfaces of a target article contained within the disinfection chamber 110.

In the present disclosure, the terms "fluence" and "irradiance" may be used interchangeably, although it is recognized that amongst the two terms, there are differences. The present disclosure, in at least some embodiments, is concerned with radiation impinging on an elemental unit of surface from one side, entering from a hemisphere of angle. That is, radiation is not reaching the surface from the rear as it is blocked by the target object. Inbound radiation can impinge on the surface substantially normal (i.e., perpendicular) to the surface element, as well as at all other angles of incidence up to +/−90°. Depending on the field of view of the radiation collection optics at the front of a detector, a broad or narrow range of angles of inbound radiation may be suitable sampled. When the angle is narrow, fluence is essentially identical to irradiance.

When monitoring radiative power in a disinfecting system, it may be useful or expeditious and simpler to collect narrow angle incident radiation. When measuring radiative power at a location within the chamber to assess the amount of total (e.g., aggregated) energy impinging on a surface, a detector with a very wide angle of acceptance may be selected. Further, inlet optics on detectors may be fitted with filters to permit passage and thus measurement only of radiation of the desired disinfecting wavelength. This information is then incorporated into the algorithms and models when correcting the predicted fluence levels with those measured in the chamber or at the surface of a test device.

By characterizing the disinfection system 100 and a given target article 240, a "target article ratio" can be established between the radiation dose received at a specific point (e.g., a region of interest such as a determined "cold spot") on the target article 240 and the dose measured by sensors 130 inside the interior volume 112 of the disinfection chamber 110 (e.g., average dose, accumulated dose, point-specific dose, or the like). The proportionality of irradiance ratios in the disinfection chamber 110 are then used to adjust (e.g., increase or decrease) a base radiation dose that would acceptably disinfect a standard surface (e.g., a test carrier inoculated with a known amount of a particular pathogen, distributed over a defined surface, during disinfectant potency testing) to a determined confidence level that a sufficient dose of radiation is received at the surface of the target article 240 (e.g., an ultrasound probe) intended for disinfection.

Disinfection of target article 240 placed in the center of the disinfection chamber 110 is achieved when the surfaces of the target article 240 that are intended for disinfection actually receive sufficient fluence to achieve high-level disinfection (i.e., a desired log reduction of viable pathogen). The value of the fluence received at each point on the target article's surface at a particular point in time, which may be time varying, and which may be constant or remain within an acceptable range during a specified time interval, may be measured by optical instrumentation and a discrete step-wise mapping process. Embodiments of the disinfection system 100 have been characterized by such mapping where irradiance levels were measured at multiple locations. This mapping provides confirmation of the incoming radiation arriving at locations where the surfaces of particular target articles 240 (e.g., ultrasound probes) would be positioned.

In FIG. 3, the results of at least one study of effectiveness of the disinfection system 100 discussed in the present disclosure are illustrated. The inventors have performed detailed and extensive testing of such effectiveness against a number of pathogens including *Bacillus subtilis*, *Clostridium sporogenes*, and many others. Exemplary results are presented in FIG. 3, and the exact spore represented by the kill curve 300 is not relevant to the discussion. Instead, the teaching of FIG. 3 illustrates that the radiation used in the present disinfection systems kills very rapidly early in the disinfection cycle as the pathogen is directly impinged upon by the radiation. As time passes, killing off the last 2 logs of viable pathogen survivors may require extension of the disinfection cycle. One theory for this is that the pathogen entities neutralized early in the disinfection cycle physically shield surviving pathogen spores from at least some inbound radiation. Neutralizing these remaining survivors that are "buried" beneath the earliest affected spores requires longer radiation exposure.

In FIG. 3, a vertical axis 302 is a logarithmic representation of a number of viable pathogen spores present in a determined area of a target article (i.e., a negative binomial distribution of colony forming units (nb.CFU)) per target article 240 (tgtArt). A first horizontal axis 304 represents an elapse of time (e.g., a disinfection cycle duration) over which a disinfection cycle is performed. The first horizontal axis 304 is measured in seconds, but other time units could also have been selected.

A second horizontal axis 306 of the kill curve 300 in FIG. 3, which is below the first horizontal axis 304, represents an accumulation of radiation dose (e.g., energy fluence integrated over the exposure) delivered to a surface of target article 240 during a disinfection cycle. The accumulation of radiation is generally linear over time in FIG. 3, but it is recognized that other disinfection programs may alter the delivery of radiation in any way, which could change the distribution of energy fluence over time. The measure of radiation dose in FIG. 3 is disinfection or "kill units," which is purposefully a non-limiting, non-standard unit chosen for the exemplary illustration. The disinfecting action of a type of radiation may sterilize a pathogen leaving it alive but non-viable, which at least in the present disclosure means that it cannot reproduce. Hence the pathogen is disinfected, but not necessarily "dead." Within the present disclosure, the term kill unit (KU), may be understood as an accumulation of "counts" that describes the overall radiation exposure delivered in the interior volume 112 of the disinfection chamber 110 over a given cycle. On a periodic schedule (e.g., 300 milliseconds), data signals from radiation sensor circuits 130 (e.g., photodiodes) are read. These values may be corrected by one or more calibration factors and summed over the course of the radiation exposure using, for example, a processing unit of the controller 140. Accordingly, it is understood that for any given disinfection chamber 110, radiation source 120 or sources 120, radiation sensor circuit 130 or radiation sensor circuits 130, and the like, a determined amount of radiation (e.g., a total amount of radiation to a selected surface in Joules, or in some cases, an area-specific dose in e.g., Joules/cm$^2$) may be measured, calculated, or otherwise determined. In FIG. 3, however, which is not limited to any particular disinfection chamber 110, radiation sources 120, or radiation sensor circuits 130, the term, kill units, has been selected to convey the relevant teaching of FIG. 3.

Also in FIG. 3, various viable pathogen measurements 308a-308f are represented. The fitted curve 310 represents the amount of viable pathogen remaining during the disinfection cycle. Accordingly, kill curve 300 may sometimes also be referred to in the art as a "survivor curve."

As evident in FIG. 3, one reason to deliver a high-power dose of radiation is to shorten a disinfection cycle time. This is because radiation very rapidly kills/disinfects a substantial portion of the pathogen early in the disinfection cycle. By applying radiation at high power levels, the energy can be delivered quickly, which can shorten the disinfection cycle time. This has the added advantage of reduced opportunity for thermal heating of the target article 240. In FIG. 3, a mean 5 log 10 reduction of pathogen is achieved in the first 150 seconds via delivery of about 5000 KU, and a mean 6 log 10 reduction of viable pathogen is achieved in after only 650 seconds and delivery of about 9300 KU.

Certain notable findings were made during testing, some of which are represented in FIG. 3. First, disinfection via UV radiation displays an extremely "front loaded" kill curve with the majority of the germicidal effect occurring in the first tens of seconds of exposure. Second, no additional growth of pathogen was observed on the target article 240 after being irradiated even when the target article 240 was first heavily inoculated with the pathogen (i.e., 7×10$^6$ spores). Third, in addition to rapidly reducing the pathogen population to a low level, the disinfection system 110 is also effective at killing a large percentage of viable pathogen spores on a target article 240. And fourth, as evident after 1600 seconds, a very small number of viable pathogen spores may still survive the disinfecting radiation dose (e.g., measurement 308*f*). In the limit of a very long exposure, disinfection becomes "sterilization," which is where no viable entities remain.

Turning back to FIG. 2, each radiation source 120 may emit radiation light rays according to its own parameters and characteristics. For example, the age of a radiation source 120 may be directly related to the light emitting characteristic thereof. Further, the time lapse after a radiation source is turned on may also affect the UV-C radiation emitted from the radiation source 120. For example, the intensity of radiation light emitted by a radiation source 120 may, as part of its natural operation, be time dependent and may include a specific pattern of waveform/variations, e.g., continuous decreasing, continuous increasing, or fluctuating. Further, each radiation source 120 may include different operation states of emitting the radiated light. For example, each radiation source 120 may have characteristics that cause the respective source to radiate at different power levels even when the output power of two or more radiation sources 120 is otherwise expected to be the same. Each radiation source 120 may also emit radiation light rays at different angles, substantially parallel to each other, or a combination of attitudes in operation. And a plurality of radiation sources may be controlled with common signals and common parameters. Alternatively, two or more radiation sources may be independently controlled via independent control signals and parameters.

A disinfection chamber 110 as described herein may be configured to create a plurality of disinfection regions within the interior volume 112. In such embodiments, the disinfection chamber 110 and/or one or more target articles 240 to be disinfected can be further configured such that the one or more target articles 240 to be disinfected are positioned within the disinfection regions in selected positions, alignments, orientations, or the like. As used herein, the term "disinfection region" refers to a region within the disinfection chamber wherein a certain intensity of disinfecting radiation is delivered over the course of a disinfection operation. In specific embodiments, the interior volume 112 is coupled to one or more sources 120 of UV-C radiation, and the one or more sources 120 of UV-C radiation are selected and arranged to deliver, independently or in common, UV-C radiation to the disinfecting regions at a varying radiation intensity, namely irradiance (also referred to as "power" to or through a specific unit of area) of, e.g., at least about 1,500 $\mu W/cm^2$. In this way, via the plurality of disinfection regions and the independent or common control of radiation sources, more precise delivery of radiation may be possible within the interior volume 112 of the respective chamber.

In some embodiments, the one or more radiation sources 120 of UV-C radiation may be selected to emit UV-C light within a band selected from between about 240 nm and about 270 nm and between about 255 nm and about 265 nm. For example, one or more UV-C source(s) 120 may be selected and arranged such that one or more disinfection regions are formed within the disinfection chamber, and the radiation intensity ("irradiance") of the UV-C radiation delivered to the one or more disinfecting regions is between about 1,500 $\mu W/cm^2$ and about 5,000 $\mu W/cm^2$. In further embodiments, the one or more UV-C source(s) 120 may be selected and arranged to provide one or more disinfecting regions wherein the irradiance of the UV-C radiation delivered within the disinfection region(s) is selected from between about 1,500 $\mu W/cm^2$ and about 2,000 $\mu W/cm^2$, between about 1,500 $\mu W/cm^2$ and about 2,500 $\mu W/cm^2$, between about 1,500 $\mu W/cm^2$ and about 3,000 $\mu W/cm^2$, between about 2,000 $\mu W/cm^2$ and about 2,500 $\mu W/cm^2$, between about 2,000 $\mu W/cm^2$ and about 3,000 $\mu W/cm^2$, between about 2,000 $\mu W/cm^2$ and about 3,500 $\mu W/cm^2$, between about 2,000 $\mu W/cm^2$ and about 2,500 $\mu W/cm^2$, between about 2,000 $\mu W/cm^2$ and about 2,750 $\mu W/cm^2$, between about 2,500 $\mu W/cm^2$ and about 2,600 $\mu W/cm^2$, between about 2,500 $\mu W/cm^2$ and about 2,750 $\mu W/cm^2$, and between about 2,500 $\mu W/cm^2$ and about 3,000 $\mu W/cm^2$, or between other like values.

In some embodiments, a disinfection region created within the interior volume 112 is characterized by the delivery of disinfecting radiation at a substantially uniform irradiance within the region. As used herein in reference to a disinfecting region, the term "substantially uniform" refers to a region within which the irradiance of the disinfecting radiation does not vary by more than 10% within the entire region (i.e., the irradiance measured within the region does not vary by more than 10%). In particular embodiments, "substantially uniform surface irradiation" refers to a disinfecting region wherein the intensity at which the disinfecting radiation is delivered to the surface(s) of the article to be disinfected does not vary across any portion of those surface(s) by more than an amount selected from ±30%, ±25%, ±20%, ±15%, ±10%, and ±5% or another like value. The disinfection regions may be re-defined or custom-tuned for different types of target articles 240, different regions of target articles 240 intended for disinfection, different operational states of radiation sources 120, or for other reasons. Further, the disinfection regions may be dynamically adjusted, collectively adjusted, independently adjusted, or adjusted in some other way. For example, if it is determined that the radiation intensity variation within a disinfection region is beyond a threshold, e.g., 10%, the disinfection region may be redefined into two or more disinfection regions according to a generated disinfection program, for example, or by some other logic.

Though disinfection does not require that radiation be delivered uniformly, it may be useful to have reasonably uniform irradiance in a local volume/region within which a target article 240 is positioned. A uniform distribution may be used to confirm the actual power level that is established where one or more surfaces of a target article 240 are being disinfected. For example, when a selected volume or region is uniformly irradiated, the radiation dosage reaching one or more surfaces in the selected volume or region may be inferred from a sensor measurement of radiation in the selected volume or region. In this way, a minimum dose of radiation that is determined to achieve the level of disinfection desired may be delivered to an intended surface and the chance of overexposure can be reduced.

The one or more interior walls defining the interior volume 112 of the disinfecting chamber 110 may also be configured to work in conjunction with the one or more radiation sources 120 of disinfecting radiation to deliver high intensity disinfecting radiation to the one or more disinfection regions within interior volume 112. For example, the one or more walls included in the disinfection chamber and, where included, the one or more reflective surfaces, can be configured to function in cooperation with the one or more radiation sources 120 of disinfecting radiation to provide one or more disinfection regions. In some embodiments, the interior volume of the disinfection chamber is defined by one or more sidewalls with a top and/or a bottom wall. In such embodiments, sources 120 of disinfecting radiation can be positioned on or within any sidewall, top wall, bottom wall, or at any junction between any of two or more sidewalls, a sidewall and a bottom wall, and a sidewall and a top wall. In addition, or in the alternative, a generated disinfection program may control one or more radiation sources 120 to deliver one or more desired levels of radiation to one or more different disinfection regions defined in the interior volume 112 of the disinfecting chamber 110. And the radiation intensity delivered to one disinfection region may concurrently be different from the radiation intensity delivered to another disinfection region.

The one or more walls defining the interior volume 112 of the disinfection chamber 110 can provide any one of many cross-sectional shapes for the chamber. For example, in particular embodiments, the one or more walls 230 are configured to provide an interior volume 112 having a circular or multi-sided cross section, such as a rectangular, triangular, hexagonal or octagonal cross section. In some embodiments, the disinfection chamber 110 is configured such that the interior volume 112 is defined by a plurality of walls and the cross-sectional shape of the interior volume is a rectangular parallelepiped or an octagonal parallelepiped. In still other embodiments, the interior volume 112, or portions thereof, may be shaped as a circle, a parabola, a double ellipse, or some other shape. In some cases, interior walls 230 of the interior volume 112 may be added, removed, or alternatively or in addition re-positioned so that a disinfection chamber having an interior volume defined by a first cross-sectional shape is modified to have an interior volume defined by a second, different cross-sectional shape.

Embodiments of the disinfection chamber 110 may include a reflector (not specifically shown for simplicity) totally or partially behind the one or more disinfecting radiation source(s) 120, and in such embodiments, where the source 120 of disinfecting radiation emits UV radiation and is a line source, such as, for example, a tube that emits UV-C radiation, the reflector may be parabolic, with the UV-C radiation source at or near its focus. Such a configuration can result in sending light, upon its initial reflection from the parabolic reflector, being sent out in mostly parallel rays. Of course other reflector geometries, UV radiation source locations, and resulting radiation fields are possible. Where tubes emitting UV-C radiation are used as the one or more sources of disinfecting radiation, in some embodiments, the rated total power delivered by the source tubes (i.e., UV-C fluence leaving the source, integrated over a surface area that encompasses the source) may range from about 20 W to about 200 W. The input electrical power consumed by disinfecting radiation source(s) 120 (e.g., UV tubes) is related and informative of the output UV power delivered from these sources, but it is noted that the relationship is not linear, and the relationship will generally change over time. In specific embodiments, however, the input power for UV tubes used in a disinfection chamber as described herein may be selected from, for example, 20 W, 25 W, 30 W, 35 W, 40 W, 45 W, 50 W, 55 W, 60 W, 65 W, 70 W, 75 W, 80 W, 85 W, 90 W, 95 W, 100 W, 135 W, 150 W, or another like value.

One or more sources 120 of disinfecting radiation may be positioned around the one or more sidewalls 230 of the interior volume 112 in a manner that results in radiation of a selected intensity (such as, e.g., energy of an intensity as described in relation to the disinfection regions) being delivered to the one or more disinfection regions within interior volume 112. The one or more sources 120 of disinfecting radiation can be positioned around the interior volume 112 to provide a disinfection region with a certain radiation intensity. For example, in embodiments of the interior volume 112 having one or more sidewalls, two or more sources 120 of disinfecting radiation, such as two or more sources 120 of UV-C radiation may be positioned along one or more of the sidewalls at uniformly spaced locations. In embodiments having multiple sidewalls, one or more sources 120 of disinfecting radiation may be positioned at one or more corners of the sidewalls. Where the disinfection chamber includes at least one top or bottom wall or surface, one or more sources 120 of disinfecting radiation can be positioned at a top and/or bottom wall or surface to provide a certain level of irradiance of disinfecting radiation directed into one or more disinfection regions formed within the interior volume 112. In specific embodiments, where the interior volume 112 of the disinfection chamber 110 is configured to include two or more sidewalls and a bottom wall, with a UV radiation source 120 at each corner formed between the sidewalls and at least one UV radiation source 120 positioned at the bottom wall, the input power of each corner tube may be at least 50 W, and where included, the power of the bottom one or more tubes may be at least 30 W.

To facilitate positioning of target articles 240 within the interior volume 112, the disinfection chamber 110 can be provided with a movable base, e.g., a suspension assembly, which positions one or more target articles 240, e.g., an ultrasound probe or other medical instrument, within the chamber. A suspension assembly as described herein works to position one or more articles to be disinfected consistently within the disinfection chamber. In these cases, where the disinfection chamber is designed to create one or more disinfection regions, providing a suspension assembly allows consistent, repeatable positioning of the one or more articles to be disinfected within disinfection region(s), thereby ensuring the one or more articles are subjected to high intensity radiation during a disinfection cycle.

In particular embodiments, a suspension assembly may be provided that positions a target article 240 in a central portion of the disinfection chamber, where a disinfection region of high-intensity radiation is created. In some variations, for instance, when the article is connected to a cable that may then extend out of the chamber, the suspension assembly comprises a slot at the top of the assembly that extends to a central portion of the top of the disinfection chamber. In some cases, the suspension assembly may include one or more control mechanisms arranged to receive control signals from a processing unit such as controller 140. In these or other cases, the suspension assembly may operate according to a generated disinfection program to adjust the position of a target article 240 in the disinfection chamber 110 in two dimensions (e.g., up, down, left, right), three dimensions (e.g., rotation, lateral motion), four dimensions (e.g., time dependent, motion during a disinfection cycle), or some other number of dimensions. In some cases, a suspension assembly includes registration features to help align a target article 240. In some cases, a suspension assembly is permanently or semi-permanently fixed such that the target article 240, once placed in the interior volume of the disinfection chamber 110, does not move during a disinfection cycle.

As will be appreciated, the positions of the shape and size of interior volume 112, the position, shape, and light reflective properties of reflective interior sidewalls that define interior volume 112, the amount and positions of radiation sources 120, the movement of movable base and other structural configurations of interior volume 112 may all affect the radiation intensity delivered to a disinfection region within interior volume 112. In the description herein, all such structural configurations of and/or within interior volume 112 are referred to as "structural configurations" of interior volume 112.

The number and positioning of the one or more radiation sensor circuits 130 included in the disinfection device 100 are also selected to provide rapid, high-level disinfection at a low temperature. For purposes of the present description, a sensor 132 includes any device or assembly of components that collects and measures an environmental condition. When referring to one or more radiation sensor circuits 130 for detecting disinfecting radiation within the disinfection chamber, the one or more radiation sensor circuits 130 will each be a device or assembly of components capable of collecting information regarding the disinfecting radiation present in the disinfection chamber, sensing or measuring the amount of disinfecting radiation within the disinfection chamber, and amplifying or processing the collected information regarding the disinfecting radiation. Further, in the context of the present description, a radiation sensor circuits 130 is considered to be positioned within the disinfection chamber where any component of the radiation sensor circuits 130 is capable of detecting, measuring, transmitting, processing, or communicating processed information regarding the disinfecting radiation present within the disinfection chamber, whether or not it is positioned within or directly exposed to the interior of the disinfecting chamber.

Each of the one or more radiation sensor circuits 130, other non-radiation-based circuits 132, and independent monitoring circuits 134 included in the interior volume 112 may be capable of detecting and communicating information such as a total radiation dose, a rate of exposure over time, and the like, to a processing unit of controller 140 (FIG. 1). For example, where UV-C light is used as the disinfecting radiation, the radiation sensor circuits 130 may sense the UV-C dose received by the target article 240 and/or the amount of UV-C radiation emitted by one or more UV-C sources 120 included in the disinfection device. In some embodiments, UV-C radiation sensor circuits 130 included in the disinfection devices described herein may be, or otherwise include, one or more photodiodes fixedly or movably positioned within the interior volume 112 of the disinfecting chamber 110. In these and in other embodiments, the one or more radiation sensor circuits 130 may comprise one or more light conducting components such as lenses, mirrors, filters and other optical elements used to collect radiation within the chamber, and may also comprise fiber optic cables or light pipes that conduct the collected disinfecting energy to a detector, such as a photodiode.

Radiation sensor circuits 130 may be standalone sensors or radiation sensor circuits 130 may be formed as a combination of discrete structures (e.g., a fiber optic probe (FOP) that includes at least one light conductive element and at least one photo electric sensor coupled into a common structure. In some variations, the radiation sensor circuits 130 within the disinfection chamber 110 are configured to have a band-pass optical filter or other electromagnetic filter in front of them so that only radiation in the spectrum of interest is sensed. In some embodiments, one or more radiation sensor circuits 130 may be positioned on or incorporated into the one or more articles to be disinfected. Positioning of one or more radiation sensor circuits 130 on the one or more target articles 240 to be disinfected may provide more accurate reading of the disinfecting radiation reaching the article 240. The devices described herein may include one or more radiation sensor circuits 130 that utilize, for example, multiple optical conductors positioned to monitor direct and indirect sources of the disinfecting radiation. Photonic conductors useful in the context of the devices described herein include, but are not limited to, fiber optic "cable" (suitable for conducting light over a long distance with low loss) or a simple "light pipe" formed of a glass, polymer, or other simple, optically transparent material that traps and contains light within itself and conducts the light with low loss. Where used, a "light pipe" as referenced herein is typically more suited to conducting light over short distances to prevent undesirable losses. A lens may be used to gather radiation and direct it to a detecting device, or the gathered radiation may be transported to another location for measurement.

It may be beneficial in some embodiments to include one sensor 130 or a set of radiation sensor circuits 130 to detect the global (i.e., aggregate) radiation dosage delivered to the interior volume 112 and another radiation sensor circuits 130 or set of sensors 130 to check or monitor each disinfection region, source, or other feature within interior volume 112.

In one embodiment, a disinfection system 100 is controlled by at least one processing unit of controller 140 (FIG. 1) to direct operation of a radiation source 120 with a specified power level and a specific period of time, namely to reach a determined cumulative threshold radiation dosage (e.g., a disinfection dose). For example, where UV-C radiation is used as the disinfecting radiation, in particular embodiments, the predetermined threshold dose may be selected from between about 50,000 $\mu J/cm^2$ and about 10,000,000 $\mu J/cm^2$. In certain such embodiments, the dose may be selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$, or between other like values. In further such embodiments, the dose may be selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$, or between other like values. In still further such embodiments, the dose may be selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$, or between other like values.

Figure 4:
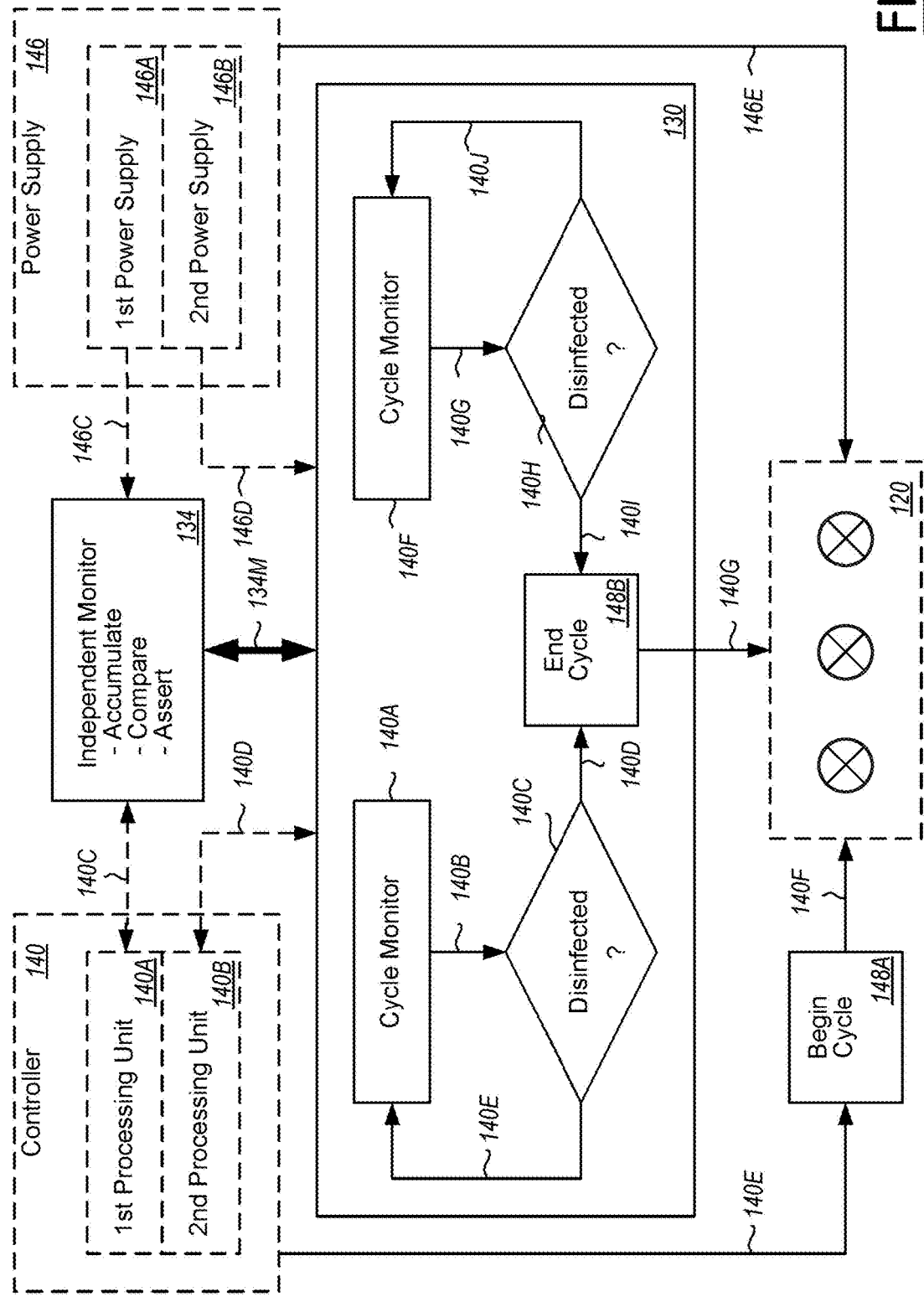
FIG. 4 is a system embodiment of a disinfection system with an independent monitor circuit.

FIG. 4 is a system embodiment of a disinfection system 100A with an independent monitor circuit. The embodiment of FIG. 4 is arranged to illustrate the flexibility of the present teaching.

In the disinfection system 100A of FIG. 4, any number of radiation sources 120 are arranged to deliver radiation into an interior volume of a disinfection chamber. Any number of radiation sensor circuits 130 are arranged to detect the radiation within the interior volume of the disinfection chamber. In the embodiment of FIG. 4, two radiation sensor circuits are illustrated, but in other embodiments, one radiation sensor circuit is present or more than two radiation sensor circuits are present.

An independent monitoring circuit 134 is arranged to monitor 134M the operations of the one or more radiation sensor circuits 130. Broadly, the one or more radiation sensor circuits 130 are arranged to determine, based on how much of the radiation is detected, when a sufficient disinfection dose has been delivered to an object in the disinfection chamber, and the independent monitoring circuit 134 will validate the proper operation of the one or more radiation sensor circuits 130.

A power supply 146 is represented in the embodiment of FIG. 4. The power supply 146 is optionally arranged to include one or more cooperative or independent power supply circuits including a first power supply circuit 146A and a second power supply circuit 146B. Power is supplied to the independent monitoring circuit 134 via a first power conduit 146C, power is supplied to the one or more radiation sensor circuits 130 via a second power conduit 146D, and power is supplied to the one or more radiation sources 120 via third power conduit 146E.

In embodiments where the independent monitoring circuit 134 and one or more radiation sensor circuits 130 share a power supply, a single power supply circuit such as the first power supply circuit 146A may provide power via the first and second power conduits 146C, 146D. If the one or more radiation sources 120 share the same power supply, then all of the circuits may receive power from a single power supply 146. Alternatively, one or more radiation sources 120 may receive power from a second power supply circuit 146B. Power is passed to the one or more radiation sources via a power conduit 146E. In at least some cases, the independent monitoring circuit 134 is implemented to satisfy a government-issued regulatory function. In such cases, it may be desirable to provide an independent source of power to each of the independent monitoring circuit 134 and the one or more radiation sensor circuits 130. One of skill in the art will appreciate that the various ones of the illustrated power supplies may be flexibly arranged, configured, and re-configured to either share power circuitry or have dedicated power supply circuitry coupled thereto.

A controller 140 is represented in FIG. 4. The controller 140 is optionally arranged to include one or more cooperative or independent processing units including a processing unit 140A and a second processing unit 140B.

Bidirectional control signals, data signals, or control signals and data signals are communicated between the controller 140 and the independent monitoring circuit 134 via a bus 140C. In at least some cases, the bus 140C includes direct, peer-to-peer communication link such as a serial peripheral interface (SPI) communication link. Other forms of bus communication means are also contemplated.

Bidirectional control signals, data signals, or control signals and data signals are communicated between the controller 140 and the one or more radiation sensor circuits 130 via a bus 140D. In at least some cases, bus 140D includes a serial communications enabled by one or more universal asynchronous receiver/transmitter (UART) circuits, which may implement communications according to any acceptable serial communication protocol (e.g., RS-232). Other forms of bus communication means are also contemplated.

In at least some cases, the disinfection device of the embodiment in FIG. 4 may be configured and optionally reconfigured in any suitable way. For example, in some cases, controller 140 may include only a single processing unit such as processing unit 140A. In these cases, the single processing unit 140A will carry out the operations of the independent monitoring circuit 134 and the one or more radiation sensor circuits 130. The single processing unit 140A in this case will manage the operations of the circuits to direct the at least one radiation source 120 to begin emitting the radiation into the interior volume of the disinfection chamber, and later direct the at least one radiation source 120 to stop emitting the radiation into the interior volume of the disinfection chamber. In this single processing unit embodiment, the single processing unit 140A may also generate an accumulated radiation value that represents an amount of the radiation detected by the at least one radiation sensor 130, and verify via the independent monitoring circuit 134 that the accumulated radiation value has reached a first radiation threshold. In at least one such case, the single processing unit 140A may execute concurrent instances of the same algorithm to generate dose information based on collected radiation data. That is a first set of radiation data may be collected by the independent monitoring circuit 134, and a second set of radiation data may be collected by the one or more radiation sensor circuits 130. The two sets of radiation data may be stored in the same or different repositories. In this way, the single processing unit 140A may independently execute a first instance of a radiation accumulation algorithm and a second instance of the radiation accumulation algorithm. The first instance of the radiation accumulation algorithm can be executed using first radiation information captured by the at least one radiation sensor circuit 130, and the second instance of the radiation accumulation algorithm can be executed using second radiation information captured by the independent monitoring circuit 130. Subsequently, the single processing unit 140A can determine a validation result based on a comparison of the first accumulated radiation value to the second accumulated radiation value, and based on the validation result, the single processing unit 140A can assert a validated disinfection signal, an error signal, or some other signal.

In other cases, as an alternative to a single processing unit carrying out the operations of both the independent monitoring circuit 134 and one or more radiation sensor circuits 130, a system may selectively separate functions of the independent monitoring circuit 134 and the one or more radiation sensor circuits 130. Such a selective separation may be based on a more efficient or otherwise improved use of computing resource, a government regulation, or some for some other reason.

In one case, a first processing unit 140A is arranged to detect and otherwise capture radiation information from the interior volume of the disinfection chamber via the independent monitoring circuit 134. The captured information may then be presented to a single processing unit of the controller 140 that carries out the disinfection operations of the disinfection chamber, including the operations of the one or more radiation sensor circuits 130, and also carries out the monitoring operations of the independent monitoring circuit 134. In this case, or in alternative cases, a second processing unit 140B may be optionally arranged to detect and otherwise capture radiation information from the interior volume of the disinfection chamber via the one or more radiation sensor circuits 130. The captured information may then be presented to a single processing unit of the controller 140 that carries out the disinfection operations of the disinfection chamber, including the operations of the one or more radiation sensor circuits 130, and also carries out the monitoring operations of the independent monitoring circuit 134.

In still other cases, a first processing unit 140A is arranged to carry out all of the computing functions of the independent monitoring circuit 134, and a second processing unit 140B is arranged to carry out all of the one or more radiation sensor circuits 130. After both the independent monitoring circuit 134 and the one or more radiation sensor circuits 130 generate values representing how much radiation was delivered into the interior volume of the disinfection chamber, any one of the processing units of controller 140 may compare the generated values and determine a validation result. In some cases, if the two independently determined radiation dose values are within ten percent (10%) of each other, then the disinfection operation is deemed a success, and a validated-disinfection-signal is asserted. In these cases, if the two independently determined radiation dose values are not within ten percent (10%) of each other, then the disinfection operation is deemed a failure. A signal indicating success or failure, as the case may be, can then be asserted.

One of skill in the art will recognized that determining a successful disinfection dose delivery may be based on any suitable "closeness" of the determined accumulated radiation value of the independent monitoring circuit 134 to the determined accumulated radiation value of the one or more radiation circuits 130. For example, in some cases, a successful determination of a valid disinfection dose delivery may be based on a closeness of two percent (2%) or less, five percent (5%) or less, or twenty percent (20%) or less. Any other desirable closeness or mechanism to determine such closeness may be implemented.

Various exemplary embodiments in context of FIG. 4 are now described.

In a first embodiment, an independent monitoring circuit 134 is coupled to a first processing unit 140A, and one or more radiation sensor circuits 130 are coupled to a second processing unit 140B. The first and second processing units 140A, 140B are separate and distinct in this embodiment, but the processors may share some or all operations in other embodiments.

In the first embodiment, a medical practitioner has started a disinfection process and a target object is in the disinfection chamber. The determination of a disinfection dose is made as described herein, and the controller 140, via one of the first and second processing units 140A, 140B, or via some other processing unit will pass communication signals 140E, 140F to direct a module 148A to begin the disinfection cycle. Upon receiving such signal, the one or more radiation sources 120 will perform local safety checks (e.g., disinfection chamber door closed, an absence of foreign objects in the disinfection chamber, and other such safety checks, and direct the one or more radiation sources 120 to begin emitting radiation.

The second processing unit will administer the operations of the one or more radiation sensor circuits 130. Concurrently, a first logic module 140A and a second logic module 140F will monitor the disinfection cycle, which may include accumulating radiation data values with first and second photodiode circuits, respectively. One or more calibration factors may be applied during the generation of an accumulated radiation value. In at least some cases, the raw or accumulated radiation values from a first radiation sensor circuit (e.g., at a first logic module 140A) may be mathematically combined with corresponding raw or accumulated radiation values from a second radiation sensor circuit (e.g., at a second logic module 140F) to generate a single accumulated radiation value representing all of the radiation received at an identified cold spot of the target object being disinfected.

Processing in a first radiation sensor circuit falls via 140B to a determination module 140C, and processing in a second radiation sensor circuit falls via 140G to a determination module 140H. The determination module or module 140C, 140H cooperate to determine whether or not the accumulated radiation value has reached a first radiation threshold. The first radiation threshold will represent the minimum dose of radiation as described in the present disclosure. If the minimum dose has been delivered (i.e., the accumulated radiation value has reached the first radiation threshold), then the controller 140 will direct a logic module 148B to direct the at least one radiation source 120 to stop emitting radiation into the interior volume of the disinfection chamber. Control is passed to the controller 140 via signals 140D, 1041, or signals 140D and 1401. The signal 140G that ends the disinfection cycle may be generated by the controller 140, the second processing unit 140B, or any other suitable processing unit. Alternatively, if the minimum dose has not been delivered, then processing in the one or more radiation sensor circuits 130 continues via control signals 140E, 140J.

Processing in the independent monitoring circuit 134 in the present embodiment is administered by the first processing unit 140A. Along the lines of the one or more radiation sensor circuits 130, the independent monitoring circuit 134 will also accumulate radiation information using, for example, a third photodiode circuit arranged to capture radiation reading from the interior volume of the disinfection chamber. The accumulated radiation information may be processed by the application of one or more calibration values, scale factors, or any other suitable adjustment mechanism.

Upon forming an accumulated radiation value, the independent monitoring circuit 134 is arranged to compare or otherwise direct the comparison of the accumulated radiation value to a corresponding accumulated radiation value from the one or more radiation sensor circuits 130 to produce a validation result as described herein. Based on the validation result, a valid disinfection signal may be asserted or an error signal may be asserted as described herein. The communication 134M between the independent monitoring circuit 134 and the one or more sensor circuits 130 may be via any suitable means. For example, the circuits may communicate via shared mailboxes, direct messages, common bus architecture, a different processing unit, or some other mean.

In another exemplary application of the disinfection system 100A of FIG. 4, the system includes a disinfection chamber 110 (FIG. 1) having an interior volume 112 (FIG. 1), a radiation source 120 configured to emit radiation into the interior volume 112 of the disinfection chamber 110, a radiation sensor circuit 130 to detect the radiation within the interior volume 112 of the disinfection chamber 110, an independent monitoring circuit 134 arranged to detect the radiation within the interior volume 112 of the disinfection chamber 110, and a computing device such as controller 140. The controller 140 includes a memory arranged to store first radiation values captured by the radiation sensor circuit 130, second radiation values captured by the independent monitoring circuit 134, and computer instructions. The computer instructions are executed by a processing unit (e.g., any one or more of controller 140, first processing unit 140A, and second processing unit 140B), which causes the processing unit to direct the radiation source 120 to start emitting the radiation into the interior volume 112 of the disinfection chamber 110. The processing unit will also generate a first accumulated radiation value based on the first radiation values stored in the memory, and generate a second accumulated radiation value based on the second radiation values stored in the memory. The processing unit will direct the radiation source 120 to stop emitting the radiation into the interior volume 112 of the disinfection chamber 110 after the first accumulated radiation value has reached a first radiation threshold. Subsequently, the processing unit will determine a validation result based on a comparison of the first accumulated radiation value to the second accumulated radiation value, and the processing unit will assert at least one of a validated disinfection signal and an error signal based on the validation result.

In some cases of the embodiment, a first photodiode is arranged in the radiation sensor circuit, a second photodiode is arranged in the radiation sensor circuit, and a third photodiode is arranged in the independent monitoring circuit. Here, in at least some cases, the processing unit is further arranged to execute the computer instructions which, when executed by the processing unit, cause the processing unit to generate the first accumulated radiation value from a mathematical combination of first radiation information captured by at least the first and second photodiodes, and generate the second accumulated radiation value from second radiation information captured by the third photodiode. In at least some of these cases, the processing unit will first apply at least one first calibration factor during the generation of the first accumulated radiation value, and apply at least one second calibration factor during the generation of the second accumulated radiation value. As noted, in at least some cases, the processing unit includes at least two different processors, and the at least two different processors include a first processor arranged to receive first radiation information from the radiation sensor circuit and a second processor arranged to receive second radiation information from the independent monitoring circuit.

Figure 5:
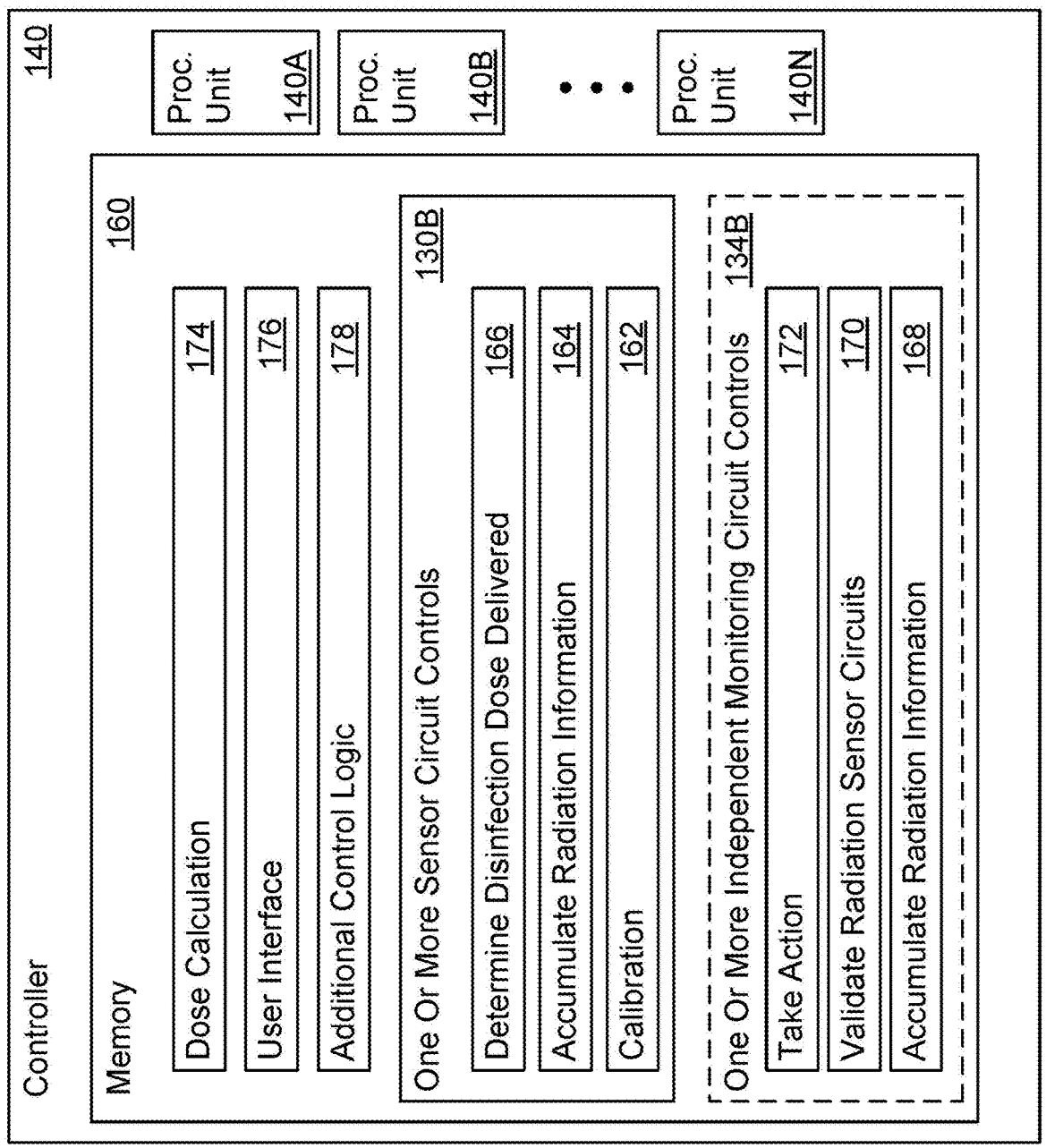
FIG. 5 is another system embodiment of a disinfection system with an independent monitor circuit.

FIG. 5 is another system embodiment of a disinfection system 100B with an independent monitor circuit. In the present disclosure, for sake of brevity, each disinfection system 100, 100A, 100B embodiment may be referred to as a disinfection system 100 except where the context of such embodiment is clearly directed to one of the embodiments discussed in the present disclosure.

In the embodiment of the FIG. 5, the disinfection system 100B includes a controller 140 embodiment and a set of hardware circuitry 180. Other components of the disinfection system 100B such as the housing, interior volume, target device hanging mechanism, and the like are included in the disinfection system 100B as would be understood by one of ordinary skill in the art, but these components are not shown to avoid obscuring the features of interest discussed in FIG. 5.

A controller 140 includes any number of processing units 140A, 140B, 140N, which for brevity may be referred to individually or collectively as a processing unit 140. The controller 140 also includes a memory 160, which may be a single memory device or a plurality of memory devices, of any suitable architecture, in any suitable arrangement. The memory 160 is along the lines of memory discussed herein, which may be local to the controller 140, remote from the controller 140, distributed amongst a plurality of computing devices, or arranged in another way.

The memory 160 includes computer instructions (e.g., software, firmware, microcode, or the like) executable by one or more of the processing units 140, parameters, and any other selected information (e.g., security information, encrypted or otherwise protected information, device identification information, default parametric information, and the like). The memory 160 includes any number of logic modules arranged to carry out the functions of the disinfection system 100B. In some cases, at least some of the logic modules are grouped or otherwise arranged. For example, memory 160 in FIG. 5 is illustrated as including one or more sensor circuit controls 130B and one or more independent monitoring circuit controls 134B. The one or more independent monitoring circuit controls 134B are represented in dashed lines indicating that such controls may optionally be arranged in the same memory as other functions of the disinfection system 100B, or the one or more independent monitoring circuit controls 134B may retain additional independence when arranged in a separate and distinct memory device.

The memory 160 may include any number of logic modules. In the embodiment of FIG. 5, the memory 160 includes at least a dose calculation logic module 174, a user interface logic module 176, and an additional control logic module 178.

The one or more sensor circuit controls 130B include logic modules to operate or otherwise control the various sensors (e.g., radiation detection sensors 130, non-radiation detection sensors 132) of the disinfection system 100B. The logic modules include a calibration logic module 162, an accumulate-radiation-information module 164, and a determine-disinfection-dose-delivered module 166.

The one or more independent monitoring circuit controls 134B include logic modules to operate or otherwise control the circuitry of one or more independent monitoring sensors. The logic modules include an accumulate-radiation-information module 168, a validate-radiation-sensor-circuits module 170, and a take-action module 172.

The disinfection system 100B of FIG. 5 includes operative hardware logic 180. The operative hardware logic 180 may include any number of radiation sources 120 and any number of radiation detection sensors 130 as described in the present disclosure, and the hardware logic 180 may further include power supply circuitry 146 (e.g., a single power supply or two or more shared or independent power supply circuits) as discussed in the present disclosure. The hardware logic may further include a user interface 182, analog-to-digital conversion (ADC) circuitry 184, any number of shared or independent clock circuits 186, and other circuits 188.

Considering logic of the disinfection system 100B, the teaching of the radiation sources 120, radiation detection sensors 130, and power supply circuitry 146 are described in other areas of the present disclosure and not repeated here. The user interface 182 hardware cooperates with the user interface logic module 176 to permit human or programmatic interaction with disinfection system 100. The interaction may be arranged to accept input such as target device identification information, timed-dose information (e.g., a manually entered time that directs how long a target device in the disinfection chamber will be exposed to radiation), and other selectable information. The interaction may be further or alternatively arranged to communicate success or failure information, history information identifying operations of the disinfection system 100, system parameters, system results, and the like. The user interface 182 and user interface control logic module 176 may include or otherwise control input/output (I/O) circuitry and user interface (UI) circuitry that includes, without limitation, serial ports, parallel ports, universal serial bus (USB) ports, IEEE 802.11 transceivers and other transceivers compliant with protocols administered by one or more standard-setting bodies, displays, projectors, printers, keyboards, computer mice, microphones, micro-electro-mechanical (MEMS) devices such as accelerometers, and the like. The user interface 182 and user interface control logic module 176 may further include or otherwise control buttons, keypads, computer mice, memory cards, serial ports, bio-sensor readers, touch screens, and the like. These devices may, for example, input control information into the system. Displays, printers, memory cards, LED indicators, temperature sensors, audio devices (e.g., speakers, piezo device, etc.), vibrators, and the like are all optionally included in the disinfection systems 100 described herein and useful to present output information to a medical practitioner operating the disinfection system 100. In some cases, the input and output devices are directly coupled to the controller 140 and electronically coupled to a processing unit 140 or other operative circuitry. In other cases, these user interface 182 devices pass information via one or more communication ports (e.g., RS-232, RS-485, infrared, USB, etc.).

The analog-to-digital conversion (ADC) circuitry 184 is used to convert analog data to digital data. In some cases, each radiation detection sensor 130 includes at least one photodiode and ADC circuitry 184 to repeatedly generate digital information that represents of the volume, strength, or other such photonic information detected and otherwise captured by the respective one or more photodiodes. Information from the ADC circuitry 184 is operatively used in at least the calibration logic module 162, accumulate-radiation-information module 164, and determine-disinfection-dose-delivered module 166. Such ADC information may also be used in the accumulate-radiation-information module 168, validate-radiation-sensor-circuits module 170, take-action module 172, and other modules of the disinfection system 100.

The disinfection systems 100 described in the present disclosure may implement any number of shared or independent clock circuits 186, Clock circuits 186 may be used to measure timed doses of radiation, to limit sensor-based disinfection cycles for safety, to control user interface operations (e.g., duration of audio output signals, a screen or display timeout, and the like), and to monitor or otherwise control other operations.

The other circuits 188 of the disinfection systems 100 described in the teaching herein may include, without limitation, door sensor circuits, illumination circuits, correct-target-device-placement circuits, foreign object detection circuits, scanner circuits, security circuits, automation circuits, memory controller circuits, and any other circuits included in the disinfection system 100.

The dose calculation logic module 174 is arranged to calculate the minimum dose of radiation as described in the present disclosure. In at least some cases, the dose calculation logic module 174 may also work cooperatively with the clock circuitry 186 and radiation sources 120 to deliver a timed dose of radiation. For example, in at least one non-limiting embodiment, a dose of disinfecting radiation is delivered for a determined period of time. The determined period of time may be selected by a medical practitioner (e.g., via user interface 182 and user interface logic module 176), selected programmatically by a remote computing device, stored in memory, or selected in another way. In such a case, the one or more independent monitoring circuits 134 and associated one or more independent monitoring circuit controls 134B may determine that a disinfecting dose has been delivered. The independent monitoring logic may, for example, calculate how much radiation was delivered and may further compare the calculated amount to one or more radiation threshold values (e.g., a first radiation threshold, a disinfection threshold value, or the like).

The dose calculation logic module 174 may be arranged to implement the minimum dose determination logic taught in the present disclosure. Accordingly, the dose calculation logic module 174 may account for determined cold spots on a particular target device, identification information representing a type of device, the placement of a target device in the disinfection chamber, the age or other parameters of the radiation sources 120, and any other information as described herein.

The additional control logic module 178 is arranged to control other operations of the disinfection systems 100 that are not otherwise described herein, but which are known to one of ordinary skill in the art. Such other operations, without limitation, may include security operations (e.g., encryption, decryption, time-in-service, calibration, fault detection, and the like), environmental sensor operations, operating system features, memory allocation and other such features, built-in-self-test (BIST) features, and the like.

The calibration logic module 162, accumulate-radiation-information module 164, and determine-disinfection-dose-delivered module 166 of the one or more sensor control circuits 130B are described throughout the present disclosure. As one of skill in the art will recognize, such features may implemented in any useful way to ensure with an acceptable level of confidence (e.g., 98% certainty, 99% certainty, 100% certainty within a statistical margin of error established by a regulatory agency, and the like) that a minimum dose of disinfection radiation has been delivered to a target device.

The accumulate-radiation-information module 168 and validate-radiation-sensor-circuits module 170 of the one or more independent monitoring circuit controls 134B are described throughout the present disclosure. As one of skill in the art will recognize, such features may implemented in any useful way to ensure with an acceptable level of confidence (e.g., 98% certainty, 99% certainty, 100% certainty within a statistical margin of error established by a regulatory agency, and the like) that the one or more radiation detection sensors 130 have accurately determined that a minimum dose of disinfection radiation has been delivered to a target device.

The take-action module 172 of the one or more independent monitoring circuit controls 134B may cooperate with the user interface 182 hardware to communicate the results of any particular disinfection cycle of other operation of the disinfection system 100. For example, the take-action module 172 may direct one or more audio, visual, tactile, or other outputs to indicate that a disinfection cycle has been successful or not successful. Additionally, or alternatively, the take-action module 172 may direct a medical practitioner that the disinfection system is ready for operation, conducting an operation, or finished with an operation. The take-action module 172 may indicate the presence or correction of a particular fault condition (e.g., door open fault, radiation source failure fault, disinfection cycle interrupted fault, system fault, foreign-object-in-chamber fault, or any other such fault).

In the foregoing disclosure, embodiments of devices, systems, and methods are described that illustrate and discuss high-level disinfection (HLD) cycles performed based on one or more of the timed delivery of radiation into a chamber, the determined dose of radiation delivered into a chamber, and the combination of time duration and determined dose of radiation delivery into a chamber. In these cases, a minimum dose of radiation is determined to be delivered to a device in the chamber, and in particular, the minimum dose of radiation is determined to be delivered to at least one region of interest (e.g., a determined cold spot) of the device. This determination may be made, at least in part, using one or more sensors arranged to control the radiation delivery means in a way that confirms, with acceptable certainty, that the correct minimum dose was delivered during the cycle.

The one or more sensors may include clock (e.g., timing) circuits, radiation measuring (e.g., photodiode) circuits, temperature circuits, foreign object detection circuits, device identification circuits, and other such circuits. In some cases, one or more sensors are radiation measuring circuits (e.g., radiation sensor circuits, independent monitoring circuits, and the like) arranged to capture instantaneous radiation measurements, radiation measurements accumulated over time, or some other data that represents instantaneous or accumulated radiation. Hence, using the sensors and a cooperating control circuit (e.g., a processing unit), the determined minimum dose can be delivered. In one case, for example, one or more sensors are configured to turn on and turn off the radiation source based on a length of time that defines a determined radiation delivery cycle. In another case, one or more sensors are configured to turn on and turn off the radiation source based on an accumulation of radiation until delivery of the minimum dose is determined. In still another case, one or more sensors are configured to identify the device placed in the chamber, and the identification information is used, at least in part, to control the radiation source over the radiation delivery cycle. In yet one more case, one or more sensors are configured to determine whether the device is correctly placed in the chamber in a specific orientation, position, and the like, and information from such sensors is used, at least in part, to control the radiation delivery cycle.

Various methods, devices, and systems have been set forth to provide details of certain exemplary and non-limiting embodiments. Various features of the embodiments are optional, and aspects of one embodiment may be suitably combined with other embodiments.

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

In the context of the embodiments described herein, it may be helpful to an understanding thereof to first set forth definitions of certain terms that are used hereinafter.

The terms "minimum dose," "minimum radiation dose," "minimum dose of radiation," and the like, are used, in all their grammatical forms, throughout the present specification and claims, to refer to the amount of radiation (e.g., a radiation field intensity, a disinfection exposure, or the like) delivered into a chamber sufficient to reduce a population of undesirable biological pathogen (organisms, cells, spores, bacterium, or the like) by a determined acceptable amount. The minimum dose may be determined and delivered using any appropriate mechanism or method. The minimum dose of radiation to which a specified surface or location is exposed (i.e., the disinfection exposure) results in at least the desired level of disinfectant action, which may be by way of sterilization, killing, or other disablement of the targeted pathogens present on a specified surface or location. In the present application, the minimum dose of radiation is inclusive of, but not limited to, factors such as angle of incidence of incoming radiation with respect to the impacted surface, absorbance, reflectance, and properties of the pathogen itself that may affect the volume of radiating photons that perform a disinfecting action on the subject pathogen, regardless of whether or not such factors are expressly accounted for. Accordingly, the minimum dose may be understood as an aggregated dose of radiation delivered into a chamber or otherwise imposed on a subject surface. In particular and without limiting the foregoing, a minimum dose refers to a number or volume of kill units. The number or volume of kill units represents an amount of radiative energy (e.g., fluence) passing through a given elemental area or volume in all directions. The amount of energy may be measured, for example, in Joules (J), Joules per square centimeter (J/cm$^2$), Joules per second (Watts), or any other suitable unit of measure.

Devices and systems are described that effectively control the disinfection exposure of radiation provided (e.g., generated, supplied, delivered, or the like) in a disinfection chamber. In this way, a selected or otherwise desired minimum exposure (i.e., minimum dosage) of radiation is delivered to a target article at each surface portion where disinfection is desired. Along these lines, one or more surface portions of the target article may be identified. A "hot spot," for example, may be identified as a portion that receives more radiation than other regions of the target article (e.g., the hot spot is a portion closer to a radiation source than other portions or in direct line-of-sight of a radiation source). A "cold spot," for example, may be identified as a portion that receives less radiation than other regions of the target article (e.g., the cold spot is a portion further from a radiation source, out of direct line-of-sight of a radiation source, shadowed by one or more features of the target article or as a result of the shape of the target article, shadowed based on a position or orientation of the target article in the disinfection chamber, or the like).

In some cases, it may be desired that at least a minimum dose of disinfecting radiation is delivered to each and every potentially contaminated and exposed surface, intended for disinfection, of the target article so as to ensure with acceptable confidence that the desired level of disinfection is achieved. A disinfection operation is conducted to achieve the determined target disinfection exposure. The disinfection operation is directed by a processor associated with the disinfection chamber executing a program, which may at least in some cases be generated in part from a model of the disinfection chamber, a model of the target medical device, and one or more radiation intensity maps. The disinfection operation is monitored by sensors on board the disinfection chamber, and the monitored data (e.g., temperature data, radiation intensity data, time data) is further used to control the disinfection operation. With techniques along these lines, the disinfection operation achieves the desired level of disinfection of all surfaces intended for disinfection, and the operation is not unnecessarily prolonged. In this way, by directing the disinfection process to be as short as reasonably possible, the utility rate of the disinfection system is improved, and further, unnecessary risk of excess radiation exposure-derived damage to disinfected medical instruments is avoided.

In embodiments described herein, with the determined minimum dosage, the temperature within the disinfection chamber is maintained at an appropriately low level. One benefit of maintaining the temperature inside the disinfection chamber at a low level is that damage to the medical instrument will be reduced by avoidance of prolonged exposure to disinfecting radiation. It is known that in the presence of intense radiation exposure, elevated temperatures may accelerate deleterious effects such as aging, crazing, cracking, hardening, softening, oxidizing, or otherwise chemically or physically altering, including discoloration, of the materials that comprise the target article. Hence, another benefit of maintaining the interior volume of the disinfection chamber at low temperature is to avoid or reduce such discoloration and aging. In some cases, for example, the generated program for the disinfection chamber may provide a minimum dose of radiation and may provide monitoring the temperature in the disinfection chamber to not exceed 35° C. to 55° C.

Though not limited in application to critical and semi-critical medical devices, the disclosed methods, devices, and systems are particularly suited to high-level disinfection of reused medical devices and instruments, including, for example, ultrasound, endotracheal, and other endocavity probes. In particular embodiments, the devices and systems described herein utilize ultra-violet ("UV") radiation to rapidly accomplish high-level disinfection without generating unacceptably high temperatures on the surface of and within the articles being processed. Many medical instruments are comprised of polymeric materials, and it is known that heating of polymers can accelerate potential damage or degradation that may result from exposure to radiation during the disinfection process. Applied use of the systems and methods disclosed herein reduce the likelihood of such damage or degradation.

In at least some cases, the disinfection chamber is further arranged to reduce damage to disinfected objects by pre-treating the chamber prior to radiative disinfection. It is known, for example, that oxygen may negatively affect polymer-based materials. Pretreatment may include, for example, purging oxygen from the disinfection chamber by flushing the chamber with nitrogen, filling the chamber with a neutral (e.g., inert) gas such as argon, or taking one or more other pretreatment actions.

A disinfection chamber of the disclosure may include a housing having a plurality of sidewalls, a top, and a door providing access to the disinfection chamber. The disinfection chamber itself may also include at least one wall defining an interior volume, and in some embodiments, the disinfection chamber will include a plurality of sidewalls, a base, and a top having an open central portion. Where the method and device utilize UV radiation, the disinfection chamber may include one or more reflective interior surfaces, one or more sources of UV radiation ("radiation source"), such as, for example, one or more sources of UV-A, UV-B, or UV-C radiation, and one or more radiation sensors. Reflective materials suitable for use in a disinfection chamber as described herein include, for example, aluminum Grand Brilliant by ALMECO GROUP, polytetrafluoroethylene (PTFE), polyvinyl alcohol (PVA), barium sulfate-containing paints, or combinations thereof. Other materials, for example, the reflective materials disclosed in U.S. Pat. No. 3,956,201 at Col. 2, Lines 56-61 and in the examples of Col. 7, Line 50-Col. 12, Line 2 and in other places and in U.S. Pat. No. 3,764,364 at Col. 2, Line 70-Col. 3, Line 20 and in other places, the contents of which are incorporated herein by reference, may also be employed. In order to facilitate placement and disinfection of articles to be processed within the disinfection chamber, the chamber may also include a suspension assembly for hanging, containing, or otherwise maintaining the article to be disinfected in a desired position within the disinfection chamber.

The disinfection chamber is sized and configured to help achieve disinfection of the articles placed therein within a desirable, and in some cases selectable, period of time such that surfaces of the articles are exposed to a desired level of radiation, referred herein as "dosage." As appreciated, a level of radiation exposure (i.e., a "dose") relates to both the radiation intensity and the time duration of exposure. For example, the target article to be disinfected, UV radiation source(s), and/or UV radiation sensor(s) may be positioned (e.g., introduced, interposed, suspended, or located) within the disinfection chamber at stationary or non-stationary locations that improve exposure of the article to radiation via controlled transmission of radiation from the sources. That is, any one or more of the target article, hangers or other target article positioning devices, sensors, radiation source(s), including one or more of direct sources of UV radiation, and indirect sources of UV radiation (e.g., dedicated reflectors of radiation rays), may be non-stationary during a disinfection cycle. In such embodiments, the disinfection chamber is configured and operated such that one or more of the article, a direct source(s) of UV light, and/or an indirect source(s) of UV light is moved (e.g., rotated in one or more planes, raised and lowered, and the like) within the disinfection chamber during a disinfection cycle to better expose each of the surface portions of the article to selected disinfecting levels of UV radiation, namely the minimum dosage.

In at least some cases, a determination that a minimum dose of radiation has been delivered is facilitated via radiation sampled in the chamber, at the target device, or in the chamber and at the target device during the disinfection process. The radiation may be directly collected/sampled, or indirectly sampled after transport, by various means to a detector or array of detectors. The one or more detectors may reside within or outside the disinfection chamber. Mirrors or other reflective surfaces, lenses, light pipes, optical fiber cables, or any other optics may be used to facilitate delivery of a representative radiation "signal" from within the chamber to the one or more sensors. Radiation collection may be narrow, moderate or wide field of view depending on the incoming angles of incidence of the radiation that is preferably collected. Since the detector may be emulating an exposed surface of a target object, it may be advantageous to use a detector with a very wide angle of acceptance to collect (e.g., sample, measure, or the like) incident radiation. In other cases, it may be preferred to use an integrating sphere or other optical collector with a similar function to attempt to sample radiation from all directions of incidence. In other cases it may be preferred to limit the angle of incidence to inbound radiation traveling toward the detector within a narrow range of incident angles.

Other factors may optionally be considered when determining a minimum dose for a specific target article. Some of these optional factors, which may be described in more detail, include the number of UV radiation sources and their associated radiation emitting characteristics (e.g., input power, output intensity of UV radiation instantaneously and over time, age of radiation source, and the like). Still other optional factors that may be considered are the inclusion or selection of material used to create one or more reflective surfaces, the size and shape of the disinfection chamber, the size and shape of the target article, the orientation and positioning of the target article, whether or not the target article or any structures within the disinfection chamber can be moved during a disinfection protocol, and any other such factors.

In the description herein, the term "radiation source" is generally used to refer to any source of radiation, including direct radiation source and/or indirect radiation source arranged in association with a disinfection chamber. The determination of a disinfection exposure may consider the exposure of a target article to all radiation sources. For example, the age of the radiation source, the fluctuation of the radiation output intensity, the characteristic frequency/ wavelength range of radiation light emission, and the time dependent variation of radiation output may all, separately or in combination, be characterized for a radiation source (i.e., the "quality" of a radiation source) and factored in the determination of the disinfection exposure.

The structural configurations and radio-optical characteristics of an interior volume of a disinfection chamber are also identified and factored in the determination of the radiation dosage. In an example, the structural configuration of the interior volume is identified in relation to a target article to be positioned within the interior volume and the radiation source(s) coupled to emit radiation rays within the interior volume. For example, the structural configuration of the interior volume and the positioning of the target article will affect an angle of radiation rays directly and/or indirectly reaching a portion of the target article, which in turn affects the radiation intensity on the portion of the target article.

In order to facilitate positioning of target articles to be processed within the disinfection chamber, the disinfection chamber may also include an attachment mechanism, such as a suspension assembly, for hanging, containing, or otherwise maintaining the target article to be disinfected in a stationary or non-stationary selected position, alignment, and/or orientation within the interior volume of the disinfection chamber. Any suitable configuration for such assembly can be utilized. For example, the assembly may be configured to suspend the article under the influence of gravity from a central portion of the top of the disinfection chamber. In other variations, an attachment mechanism may be provided that couples, in a removable manner, the article to an assembly or wall within the disinfection chamber and/or positions and orients the article within the disinfection chamber. Said attachment system may be applied to, or interact with, a region on the target article that is not targeted for disinfection. For example, on the cable of a probe that is attached to an imaging system, or on a region of an independent (e.g., unattached) device that is considered non-critical and thus does not require disinfection treatment. Even further, an attachment mechanism suitable for use in the disinfection chamber may comprise a pair of, pairs of, or sets of complementary mating elements. Assemblies for restraining, maintaining, or positioning an article within the disinfection chamber may optionally include components made of UV transparent material so as to restrain the article but not interfere with passage of the disinfecting UV radiation. Configurations might include tubes, holding forks, positioning surfaces, or any other suitable structures. These assemblies may be arranged fixedly to receive the article, or they may translate and rotate, or otherwise move into position, be movable, for example, in a clamshell manner, or in combination with movement of the target article, so as to come together to capture, fixate, or trap the article to be disinfected.

Systems according to the present disclosure include a disinfection device having a disinfection chamber and one or more radiation sources as described herein operated to achieve disinfection of one or more target articles. In specific embodiments, the disinfection device is operated according to a generated disinfection program (e.g., an algorithm, a protocol, a software program, or the like) that will deliver the determined minimum dose of radiation as described herein. In such embodiments, one or more target articles are positioned within the disinfection chamber of the disinfection device, and exposure of the one or more articles to an environmental condition capable of disinfecting the articles (e.g., exposure to UV radiation) is initiated based on the determined disinfection exposure, which includes radiation intensity and exposure duration. Once the disinfection condition is initiated/imposed, one or more inputs can be collected and processed according to the generated disinfection program.

In specific embodiments, systems according to the present description are operated according to one or more algorithms of the generated disinfection program for determining, calibrating, or adjusting one or more of the system conditions that cooperate to deliver the determined minimum dose to the target article. The one or more algorithms may include provisions to determine whether the minimum dose has been reached on all portions of a target article intended for disinfection. The one or more algorithms may be arranged to determine where, when, and how the disinfection conditions may be terminated (i.e., the "termination point" or "point for termination"). The one or more algorithms may be arranged to extend the process for irradiating the target article, or for signaling a point at which the disinfection conditions are terminated in order to avoid unwanted damage to the one or more target articles being processed. The information processed according to the one or more algorithms and utilized by the systems described herein may include, for example, determinations of exposure to a disinfecting condition, the temperature at various locations within the disinfection chamber or at the surface of the target articles being disinfected, and time over which articles are exposed to a disinfecting condition. Information collected may be processed in ways to improve the accuracy of data measurements. For example, measured UV exposure may be integrated, averaged, or otherwise consolidated across multiple sensors appropriately reporting/representing the disinfecting power level present within the disinfection chamber. Additional examples of information that can be collected via monitors, sensors, or another input mechanism (e.g., timer, user input parameters, or the like) and then processed by one or more algorithms utilized in operating a system as described herein including the operational status and/or output of UV radiation sources, their level of cleanliness, the presence or absence of internal reflective or absorptive surfaces, the status or responsiveness of UV radiation sensor(s), and other factors that may induce variability in the disinfection conditions over time. Dirtiness of the surface of a target article, or some other assessment of the target article's condition, and thus suitability for disinfection, may also be assessed by one or more detectors to ensure the article has, for example, been pre-cleaned properly before disinfection.

The disinfection system can be operated manually such that one or more operators are directed by a generated disinfection program to load one or more test articles within the disinfection device, initiate a disinfection cycle, monitor the system parameters necessary for execution of an algorithm utilized to determine the termination point for the cycle, and terminate the disinfection cycle according to the algorithm. The disinfection system can be operated semi-automated such that one or more of the tasks required for operation, such as, for example, monitoring of the system parameters, applying an algorithm to determine the termination point for a given disinfection cycle, or terminating a disinfection cycle, is automated or otherwise directed by a generated disinfection program. Additionally, or in the alternative, the disinfection system can be operated fully automated. For purposes of the present disclosure, a fully automated system is one in which, once a generated disinfection program is initiated by an operator, each of the subsequent steps through termination of the disinfection cycle are automated.

In particular embodiments, the systems disclosed herein include one or more processing units capable of executing a generated disinfection program that directs one or more algorithms that carry out the disinfection and perform other peripheral tasks. For example, in some cases, the one or more algorithms are operable to calibrate system components, monitor disinfection conditions, and terminate a disinfection cycle. In these or other cases, the one or more algorithms may optionally be arranged to analyze sensor data (e.g., digital imagery from a camera, digital data from an infrared sensor, electronic signals from mating components) to determine how the target article is placed or otherwise oriented in the disinfection chamber. In this way, the algorithm can assess any number of hot spots on the target article, cold spots on the target article, or other regions of interest on the target article along with the current condition/state of the disinfection chamber to deliver radiation. Based on the assessment, the algorithm can calculate an appropriate minimum dose of radiation in real time and adjust the generated disinfection program accordingly. This beneficial analysis can account for the fact that a target article might not be positioned in the disinfection chamber exactly in the same way or location each time. And if by the assessment the algorithm determines that a target article is too far out of position (e.g., too high, too low, rotated unfavorably, or the like) to effect a suitable minimum dose of radiation, the system can alert a user of the errant condition, thereby permitting the user to correct the problem (e.g., reposition the target article, re-start the algorithm, adjust other parameters, or the like). In some cases, the system is provided with an ability to reposition the target automatically, manually, or automatically and manually. In these or other cases, the system is provided with an ability to adjust the radiation sources to supply more or less radiation to the chamber in a spatially preferred manner and thus to compensate for the errant position.

In some embodiments, one or more algorithms of the generated disinfection program assess and/or determine the point of termination for a disinfection cycle based on one or more system conditions. For example, measurements may be taken from one or more sensors throughout the disinfection cycle of at least: 1) an average of or point exposures to a disinfecting condition, measured from one or more sensors, 2) total exposure to a disinfecting condition as measured from one or more sensors, 3) a combination of average exposure to a disinfecting condition measured by one or more sensors considered together with total exposure to the disinfection condition measured at one or more sensors, 4) duration or elapsed time of actual exposure to a disinfecting condition, 5) temperature, such as one or more of a temperature measured within the disinfection chamber and/or at one or more surface temperatures at positions of interest on the target article subjected to the disinfection cycle, and 6) the operating conditions of system components, such as, for example, one of more radiation sources or sensors.

In some cases, one or more sensors may also interrogate the surface of the target article to determine its level of cleanliness. Methods for rapid, high-level disinfection of target articles are also provided herein. Methods disclosed can be carried out under conditions that are less prone to damage or degrade the one or more articles being disinfected. For example, using UV radiation, methods according to the present disclosure can accomplish a "rapid" high-level disinfection of a medical device in a matter of minutes (e.g., less than 10 minutes), while maintaining conditions such that the surface temperatures of target devices being disinfected do not exceed a selected upper threshold, for example, no more than 55° C. In even more specific embodiments, the methods described herein may use UV-C radiation to accomplish the selected high-level of disinfection within a time period considered acceptably short (i.e., "rapid") to make the disinfected device available for reuse in the clinical or treatment setting. Times of a rapid high-level disinfection of a target medical device include from 5 minutes or less, 3 minutes or less, 1.5 minutes or less, and 1 minute or less. The rapid disinfection cycle times provided by methods described herein can lead to improved productivity and compliance with the disinfection protocols, and also avoid undesired thermally accelerated radiation (e.g., UV) degradation of the target articles being disinfected.

The chosen or otherwise determined minimum dosage of radiation exposure according to the present disclosure serves to provide acceptable disinfection and serves to mitigate or otherwise reduce degradation of component materials and or joints or connections between components of the test articles being disinfected. The methods, devices, and systems provided are suited to eliminating a non-limiting, non-exhaustive range of microorganisms ("contaminants"), including, for example, *mycobacterium* species, *Escherichia coli, Staphylococcus aureus, Tricophyton mentagrophytes, Pseudomonas aeruginosa, Enterococcus hirae, Bacillus subtilis, Bacillus cereus, Clostridium sporogenes, Candida albicans*, orthopoxvirus, enterovirus, adenovirus type 5, and human papilloma virus. As appreciated, the minimum dosage may be calculated based on any one or more of the radiation intensity map, the type of contaminants, the disinfection requirement and characteristics of the target article, the characteristics of the disinfection chamber, measured and/or calculated real-time data (e.g., sensor data), and other such factors as discussed in the present disclosure.

Methods for determining acceptable disinfection conditions for a given target article, microorganism, or type of contamination are also provided. In order to better identify the conditions required for disinfection and to reduce the potential for undesired over-exposure or under-exposure of articles to disinfection conditions, methods described herein provide for setting and confirming operational parameters of the disinfection devices and systems described herein using test data collected for targeted microorganisms. For example, in specified embodiments, testing of one or more pathogens of interest is conducted, wherein a known amount of selected pathogen(s) (e.g., live bacteria, dormant spores, fungi, molds, viruses, and the like) is exposed to a controlled disinfection condition (e.g., a known dose of UV radiation, in energy delivered per unit area). The known amount of the selected pathogen(s) can be deposited on a substrate, such as a glass/polymeric/ceramic/metal substrate, and exposed to UV radiation delivered from a UV source positioned to provide a known and controlled dose of UV radiation. At least one example of systems and devices to perform such pathogen testing is disclosed in PCT/US2017/043264, entitled Bioassay Carrier And Preparation Thereof, filed Jul. 21, 2017, and assigned to the same assignee as the present application, which application is incorporated by reference into the present disclosure.

A radiation source may be operated such that it delivers radiation energy of the desired disinfecting wavelengths at a constant or otherwise controlled rate measured in Joules/second (i.e., Watts), or some other unit of measure, and delivers radiation energy for a selected or selectable amount of time (e.g., seconds) to achieve the selected radiation dose.

In the study of photonics and radiation, it is known to define a reference area in meters squared ($m^2$) or centimeters squared ($cm^2$) upon which the radiation impinges, or through which it passes. In these courses of study, the power level per unit area, or irradiance, which is sometimes also called "fluence," is defined in Watts/$cm^2$. In such embodiments, for example, the target article can be irradiated directly from one direction, such as above, with incident radiant energy measured at the plane of the target article substrate. The conditions required to achieve a certain logarithmic reduction in the population of viable pathogen(s) being evaluated provide starting conditions for setting the system parameters and disinfection cycle times for the disinfection systems described herein. Using such information, the disinfection cycle conditions are then confirmed in the actual disinfection system via one or more test runs with test articles which are inoculated, disinfected, and then assayed to determine disinfection efficacy. Depending on the results achieved with the starting conditions to obtain the desired disinfection, target dose and other conditions can be adjusted to achieve the desired level of disinfection (i.e., the minimum required dose to all surfaces intended for disinfection), without needlessly risking overexposure of the target article to the disinfecting conditions.

The devices and systems described herein may be configured to allow calibration of the one or more sources of disinfecting radiation and/or the one or more detectors of disinfecting radiation. For example, in some cases, the disinfection chamber may be configured to allow for placement of one or more calibrating sensors and additionally or alternatively one or more calibration articles that emulates an actual target device. In these cases, an assessment of the real time irradiance level and/or total dose of disinfecting radiation energy (i.e., the integral of the radiant power over time) delivered to one or more regions within the chamber or one or more surface portions of a target calibration article can be made.

In particular embodiments, the systems disclosed herein include one or more processing units capable of executing a generated disinfection program that directs one or more algorithms that carry out the disinfection and perform other peripheral tasks. For example, in some cases, the one or more algorithms are operable to calibrate system components, monitor disinfection conditions, and terminate a disinfection cycle. In these or other cases, the one or more algorithms may optionally be arranged to analyze sensor data (e.g., digital imagery from a camera, digital data from an infrared sensor, electronic signals from mating components) to determine how the target article is placed or otherwise oriented in the disinfection chamber. In this way, the algorithm can assess any number of hot spots on the target article, cold spots on the target article, or other regions of interest on the target article along with the current condition/state of the disinfection chamber to deliver radiation. Based on the assessment, the algorithm can calculate an appropriate minimum dose of radiation in real time and adjust the generated disinfection program accordingly. This beneficial analysis can account for the fact that a target article might not be positioned in the disinfection chamber exactly in the same way or location each time. And if by the assessment the algorithm determines that a target article is too far out of position (e.g., too high, too low, rotated unfavorably, or the like) to effect a suitable minimum dose of radiation, the system can alert a user of the errant condition, thereby permitting the user to correct the problem (e.g., reposition the target article, re-start the algorithm, adjust other parameters, or the like). In some cases, the system is provided with an ability to reposition the target automatically, manually, or automatically and manually. In these or other cases, the system is provided with an ability to adjust the radiation sources to supply more or less radiation to the chamber in a spatially preferred manner and thus to compensate for the errant position.

In some embodiments, one or more algorithms of the generated disinfection program assess and/or determine the point of termination for a disinfection cycle based on one or more system conditions. For example, measurements may be taken from one or more sensors throughout the disinfection cycle of at least: 1) an average of or point exposures to a disinfecting condition, measured from one or more sensors, 2) total exposure to a disinfecting condition as measured from one or more sensors, 3) a combination of average exposure to a disinfecting condition measured by one or more sensors considered together with total exposure to the disinfection condition measured at one or more sensors, 4) duration or elapsed time of actual exposure to a disinfecting condition, 5) temperature, such as one or more of a temperature measured within the disinfection chamber and/or at one or more surface temperatures at positions of interest on the target article subjected to the disinfection cycle, and 6) the operating conditions of system components, such as, for example, one of more radiation sources or sensors.

In some cases, one or more sensors may also interrogate the surface of the target article to determine its level of cleanliness. Methods for rapid, high-level disinfection of target articles are also provided herein. Methods disclosed can be carried out under conditions that are less prone to damage or degrade the one or more articles being disinfected. For example, using UV radiation, methods according to the present disclosure can accomplish a "rapid" high-level disinfection of a medical device in a matter of minutes (e.g., less than 10 minutes), while maintaining conditions such that the surface temperatures of target devices being disinfected do not exceed a selected upper threshold, for example, no more than 55° C. In even more specific embodiments, the methods described herein may use UV-C radiation to accomplish the selected high-level of disinfection within a time period considered acceptably short (i.e., "rapid") to make the disinfected device available for reuse in the clinical or treatment setting. Times of a rapid high-level disinfection of a target medical device include from 5 minutes or less, 3 minutes or less, 1.5 minutes or less, and 1 minute or less. The rapid disinfection cycle times provided by methods described herein can lead to improved productivity and compliance with the disinfection protocols, and also avoid undesired thermally accelerated radiation (e.g., UV) degradation of the target articles being disinfected.

The chosen or otherwise determined minimum dosage of radiation exposure according to the present disclosure serves to provide acceptable disinfection and serves to mitigate or otherwise reduce degradation of component materials and or joints or connections between components of the test articles being disinfected. The methods, devices, and systems provided are suited to eliminating a non-limiting, non-exhaustive range of microorganisms ("contaminants"), including, for example, *mycobacterium* species, *Escherichia coli, Staphylococcus aureus, Tricophyton mentagrophytes, Pseudomonas aeruginosa, Enterococcus hirae, Bacillus subtilis, Bacillus cereus, Clostridium sporogenes, Candida albicans*, orthopoxvirus, enterovirus, adenovirus type 5, and human papilloma virus. As appreciated, the minimum dosage may be calculated based on any one or more of the radiation intensity map, the type of contaminants, the disinfection requirement and characteristics of the target article, the characteristics of the disinfection chamber, measured and/or calculated real-time data (e.g., sensor data), and other such factors as discussed in the present disclosure.

Methods for determining acceptable disinfection conditions for a given target article, microorganism, or type of contamination are also provided. In order to better identify the conditions required for disinfection and to reduce the potential for undesired over-exposure or under-exposure of articles to disinfection conditions, methods described herein provide for setting and confirming operational parameters of the disinfection devices and systems described herein using test data collected for targeted microorganisms. For example, in specified embodiments, testing of one or more pathogens of interest is conducted, wherein a known amount of selected pathogen(s) (e.g., live bacteria, dormant spores, fungi, molds, viruses, and the like) is exposed to a controlled disinfection condition (e.g., a known dose of UV radiation, in energy delivered per unit area). The known amount of the selected pathogen(s) can be deposited on a substrate, such as a glass/polymeric/ceramic/metal substrate, and exposed to UV radiation delivered from a UV source positioned to provide a known and controlled dose of UV radiation. At least one example of systems and devices to perform such pathogen testing is disclosed in PCT/US2017/043264, entitled Bioassay Carrier And Preparation Thereof, filed Jul. 21, 2017, and assigned to the same assignee as the present application, which application is incorporated by reference into the present disclosure.

A radiation source may be operated such that it delivers radiation energy of the desired disinfecting wavelengths at a constant or otherwise controlled rate measured in Joules/second (i.e., Watts), or some other unit of measure, and delivers radiation energy for a selected or selectable amount of time (e.g., seconds) to achieve the selected radiation dose. In the study of photonics and radiation, it is known to define a reference area in meters squared ($m^2$) or centimeters squared ($cm^2$) upon which the radiation impinges, or through which it passes. In these courses of study, the power level per unit area, or irradiance, which is sometimes also called "fluence," is defined in Watts/$cm^2$. In such embodiments, for example, the target article can be irradiated directly from one direction, such as above, with incident radiant energy measured at the plane of the target article substrate. The conditions required to achieve a certain logarithmic reduction in the population of viable pathogen(s) being evaluated provide starting conditions for setting the system parameters and disinfection cycle times for the disinfection systems described herein. Using such information, the disinfection cycle conditions are then confirmed in the actual disinfection system via one or more test runs with test articles which are inoculated, disinfected, and then assayed to determine disinfection efficacy. Depending on the results achieved with the starting conditions to obtain the desired disinfection, target dose and other conditions can be adjusted to achieve the desired level of disinfection (i.e., the minimum required dose to all surfaces intended for disinfection), without needlessly risking overexposure of the target article to the disinfecting conditions.

The devices and systems described herein may be configured to allow calibration of the one or more sources of disinfecting radiation and/or the one or more detectors of disinfecting radiation. For example, in some cases, the disinfection chamber may be configured to allow for placement of one or more calibrating sensors and additionally or alternatively one or more calibration articles that emulates an actual target device. In these cases, an assessment of the real time irradiance level and/or total dose of disinfecting radiation energy (i.e., the integral of the radiant power over time) delivered to one or more regions within the chamber or one or more surface portions of a target calibration article can be made.

Example A-1 is a disinfection device, comprising: a disinfection chamber having an interior volume; at least one radiation source configured to emit radiation into the interior volume of the disinfection chamber; a processing unit arranged to execute computer instructions that, when executed by the processing unit, cause the processing unit to direct a delivery of a disinfection dose of the radiation into the interior volume of the disinfection chamber; at least one radiation sensor circuit configured to detect the radiation within the interior volume of the disinfection chamber and further configured, based on how much of the radiation is detected, to determine when said disinfection dose has been delivered; and an independent monitoring circuit arranged to validate a proper operation of the at least one radiation sensor circuit. In some cases, the processing unit processes radiation information from the independent monitoring circuit. And in other cases, a second separate and distinct processing unit processes radiation information from the independent monitoring circuit.

Example A-2 may include the subject matter of Example A-1, and alternatively or additionally any other example herein, and the computer instructions may comprise further computer instructions that, when executed by the processing unit, cause the processing unit to: direct the at least one radiation source to begin emitting the radiation into the interior volume of the disinfection chamber; generate an accumulated radiation value, the accumulated radiation value representing an amount of radiation detected by the at least one radiation sensor; verify that the accumulated radiation value reaches a first radiation threshold; and direct the at least one radiation source to stop emitting the radiation into the interior volume of the disinfection chamber.

Example A-3 may include the subject matter of Examples A-1 to A-2, and alternatively or additionally any other example herein, and further comprise: a first photodiode arranged in the at least one radiation sensor circuit the first photodiode positioned at a first location in the interior volume of the disinfection chamber; a second photodiode arranged in the at least one radiation sensor circuit the second photodiode positioned at a second location in the interior volume of the disinfection chamber; and a third photodiode arranged in the independent monitoring circuit, the third photodiode positioned at a third location in the interior volume of the disinfection chamber, wherein the first location, the second location, and the third location are different locations.

Example A-4 may include the subject matter of Example A-3, and alternatively or additionally any other example herein, wherein the second location and the third location are in close proximity to each other.

Example A-5 may include the subject matter of any of Examples A-1 to A-4, and alternatively or additionally any other example herein, wherein the processing unit is arranged to receive first radiation information from the at least one radiation sensor circuit and arranged to not receive second radiation information from the independent monitoring circuit.

Example A-6 may include the subject matter of any of Examples A-1 to A-5, and alternatively or additionally any other example herein, and further comprise: a second processing unit arranged to receive first radiation information from the independent monitoring circuit and arranged to not receive second radiation information from the at least one radiation sensor circuit.

Example A-7 may include the subject matter of any of Examples A-1 to A-6, and alternatively or additionally any other example herein, wherein the at least one radiation sensor circuit and the independent monitoring circuit communicate radiation information to different processing units.

Example A-8 may include the subject matter of any of Examples A-1 to A-7, and alternatively or additionally any other example herein, wherein the processing unit is communicatively coupled to both the at least one radiation sensor circuit and the independent monitoring circuit.

Example A-9 may include the subject matter of Example A-8, and alternatively or additionally any other example herein, and further comprise: a second processing unit communicatively coupled to only one of the at least one radiation sensor circuit and the independent monitoring circuit.

Example A-10 may include the subject matter of any of Examples A-1 to A-9, and alternatively or additionally any other example herein, and further comprise: a power supply circuit electrically coupled to only one of the at least one radiation sensor circuit and the independent monitoring circuit.

Example A-11 may include the subject matter of any of Examples A-1 to A-10, and alternatively or additionally any other example herein, and further comprise: a dedicated communication bus that couples the independent monitoring circuit to its respective processing unit.

Example A-12 may include the subject matter of any of Examples A-1 to A-11, and alternatively or additionally any other example herein, and further comprise: a dedicated communication bus coupling the independent radiation sensor circuit to a respective processing unit.

Example A-13 may include the subject matter of any of Examples A-1 to A-12, and alternatively or additionally any other example herein, and further comprise: a power supply circuit electrically coupled to both of the at least one radiation sensor circuit and the independent monitoring circuit.

Example A-14 may include the subject matter of any of Examples A-1 to A-13, and alternatively or additionally any other example herein, and further comprise: a second processing unit arranged to execute second computer instructions that, when executed by the second processing unit, cause the second processing unit to generate a second accumulated radiation value, the second accumulated radiation value representing a second amount of radiation detected by the independent monitoring circuit.

Example A-15 may include the subject matter of Example A-14, and alternatively or additionally any other example herein, wherein validating the proper operation of the at least one radiation sensor circuit includes comparing the second accumulated radiation value to the accumulated radiation value.

Example A-16 may include the subject matter of Example A-14, and alternatively or additionally any other example herein, wherein validating the proper operation of the at least one radiation sensor circuit includes determining that the accumulated radiation value and the second accumulated radiation value are within a determined validation threshold.

Example A-17 may include the subject matter of any of Examples A-1 to A-16, and alternatively or additionally any other example herein, wherein the radiation is ultraviolet radiation.

Example A-18 may include the subject matter of any of Examples A-1 to A-17, and alternatively or additionally any other example herein, wherein the radiation is ultraviolet-C radiation.

Example A-19 may include the subject matter of Example A-2, and alternatively or additionally any other example herein, wherein the further computer instructions include a radiation accumulation algorithm that accumulates radiation values representing the amount of radiation detected by the at least one radiation sensor, and wherein second computer instructions, when executed by a second processing unit, cause the second processing unit to independently execute the radiation accumulation algorithm to accumulate second radiation values representing a second amount of radiation detected by the independent monitoring circuit.

Example A-20 may include the subject matter of Example A-2, and alternatively or additionally any other example herein, wherein the processing unit and the second processing unit are different processing units.

Example B-1 is disinfection method, comprising: delivering, via at least one radiation source, a disinfection dose of radiation into an interior volume of a disinfection chamber; detecting, via at least one radiation sensor circuit, the radiation within the interior volume of the disinfection chamber; determining, based on how much of the radiation is detected, when said disinfection dose has been delivered; and validating, via an independent monitoring circuit, a proper operation of the at least one radiation sensor circuit.

Example B-2 may include the subject matter of Example B-1, and alternatively or additionally any other example herein, and delivering the disinfection dose of the radiation may comprise directing the at least one radiation source to begin emitting the radiation into the interior volume of the disinfection chamber; generating an accumulated radiation value that represents an amount of the radiation detected by the at least one radiation sensor; verifying that the accumulated radiation value has reached a first radiation threshold; and based on the verifying, directing the at least one radiation source to stop emitting the radiation into the interior volume of the disinfection chamber.

Example B-3 may include the subject matter of any of Examples B-1 to B-2, and alternatively or additionally any other example herein, and may further comprise: independently executing a first instance of a radiation accumulation algorithm and a second instance of the radiation accumulation algorithm, wherein the first instance of the radiation accumulation algorithm is executed using first radiation information captured by the at least one radiation sensor circuit, and wherein the second instance of the radiation accumulation algorithm is executed using second radiation information captured by the independent monitoring circuit.

Example B-4 may include the subject matter of Example B-3, and alternatively or additionally any other example herein, wherein the first instance of the radiation accumulation algorithm is executed via a first processing unit and the second instance of the radiation accumulation algorithm is executed via a second processing unit, wherein the first and second processing units are different processing units.

Example B-5 may include the subject matter of any of Examples B-1 to B-4, and alternatively or additionally any other example herein, wherein determining how much of the radiation is detected includes applying a calibration factor to radiation information received by at least one photodiode of the at least one radiation sensor circuit.

Example C-1 is a system, comprising: a disinfection chamber having an interior volume; a radiation source arranged to emit radiation into the interior volume of the disinfection chamber; a radiation sensor circuit arranged to detect the radiation within the interior volume of the disinfection chamber; an independent monitoring circuit arranged to detect the radiation within the interior volume of the disinfection chamber; and a computing device that includes: a memory arranged to store: first radiation values captured by the radiation sensor circuit; second radiation values captured by the independent monitoring circuit; and computer instructions; and; a processing unit arranged to execute the computer instructions which, when executed by the processing unit, cause the processing unit to: direct the radiation source to start emitting the radiation into the interior volume of the disinfection chamber; generate a first accumulated radiation value based on the first radiation values stored in the memory; generate a second accumulated radiation value based on the second radiation values stored in the memory; direct the radiation source to stop emitting the radiation into the interior volume of the disinfection chamber after the first accumulated radiation value has reached a first radiation threshold; determine a validation result based on a comparison of the first accumulated radiation value to the second accumulated radiation value; and assert, based on the validation result, at least one of a validated disinfection signal and an error signal.

Example C-2 may include the subject matter of Example C-1, and alternatively or additionally any other example herein, and the system may further comprise: a first photodiode arranged in the radiation sensor circuit; a second photodiode in the radiation sensor circuit; and a third photodiode in the independent monitoring circuit.

Example C-3 may include the subject matter of Example C-2, and alternatively or additionally any other example herein, wherein the processing unit is arranged to execute the computer instructions which, when executed by the processing unit, may cause the processing unit further to: generate the first accumulated radiation value from a mathematical combination of first radiation information captured by at least the first and second photodiodes; and generate the second accumulated radiation value from second radiation information captured by the third photodiode.

Example C-4 may include the subject matter of Example C-3, and alternatively or additionally any other example herein, wherein the processing unit is arranged to execute the computer instructions which, when executed by the processing unit, may cause the processing unit further to: apply at least one first calibration factor during the generation of the first accumulated radiation value; and apply at least one second calibration factor during the generation of the second accumulated radiation value.

Example C-5 may include the subject matter of any of Examples C-1 to C-4, and alternatively or additionally any other example herein, wherein the processing unit includes at least two different processors, the at least two different processors including a first processor arranged to receive first radiation information from the radiation sensor circuit and a second processor arranged to receive second radiation information from the independent monitoring circuit.

Example D-1 is disinfection method, comprising: delivering, via at least one radiation source, a dose of radiation into an interior volume of a disinfection chamber; determining, via at least electronic circuit, how much of the radiation has been delivered to at least a portion of a target object within the interior volume of the disinfection chamber; based on the determining, stopping delivery of the radiation into the interior volume of the disinfection chamber; and validating, via an independent monitoring circuit, a proper operation of the at least one electronic sensor circuit.

Example D-2 may include the subject matter of Example D-1, and alternatively or additionally any other example herein, and determining how much of the radiation has been delivered to at least a portion of a target object may comprise setting a value representing a duration of time in the electronic circuit; directing the at least one radiation source to begin emitting the radiation into the interior volume of the disinfection chamber; detecting an expiration of the duration of time; and based on the detecting, directing the at least one radiation source to stop emitting the radiation into the interior volume of the disinfection chamber.

Example D-3 may include the subject matter of any of Examples D-1 to D-2, and alternatively or additionally any other example herein, and validating, via the independent monitoring circuit, the proper operation of the at least one electronic sensor circuit may further comprise: independently executing a first instance of a radiation accumulation algorithm; determining an amount of radiation that has been captured by at least one radiation sensor circuit; and comparing the amount of radiation to a first radiation threshold.

Example D-4 may include the subject matter of any of Examples D-1 to D-3, and alternatively or additionally any other example herein, wherein the electronic circuit is a clock circuit.

Example D-5 may include the subject matter of any of Examples D-1 to D-4, and alternatively or additionally any other example herein, wherein the independent monitoring circuit includes at least one photodiode arranged in at least one radiation sensor circuit.

Example E-1 is disinfection method, comprising: delivering, via at least one radiation source, a dose of radiation into an interior volume of a disinfection chamber; determining, via at least electronic circuit, how much of the radiation has been delivered to at least a portion of a target object within the interior volume of the disinfection chamber; based on the determining, stopping delivery of the radiation into the interior volume of the disinfection chamber; and validating, via an independent monitoring circuit, a proper delivery of minimum dose of radiation to at least the portion of the target object.

Example E-2 may include the subject matter of Example E-1, and alternatively or additionally any other example herein, wherein the independent monitoring circuit includes at least one photodiode arranged in at least one radiation sensor circuit.

Having now set forth certain embodiments, further clarification of certain terms used herein may be helpful to providing a more complete understanding of that which is considered inventive in the present disclosure.

In the embodiments of present disclosure, one or more particular components of a disinfection system are shown in the various figures and described in the present disclosure. The various components and devices of the embodiments are interchangeably described herein as "coupled," "connected," "attached," and the like. It is recognized that once assembled and operated, the system is suitably sealed to prevent radiation from escaping the system. The materials and the junctions formed at the point where two or more structures meet in the present embodiments are sealed to a mechanically, medically, or otherwise FIG. 4 includes a data flow diagram illustrating a non-limiting process that may be used by embodiments of a disinfection system 100. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

The figures in the present disclosure illustrate portions of one or more non-limiting computing device embodiments such as one or more components of controller 140. The computing devices may include operative hardware found in conventional computing device apparatuses such as one or more processors, volatile and non-volatile memory, serial and parallel input/output (I/O) circuitry compliant with various standards and protocols, wired and/or wireless networking circuitry (e.g., a communications transceiver), one or more user interface (UI) modules, logic, and other electronic circuitry.

The computing devices described herein have electronic memory accessible by at least one processing unit within the device. The memory is programmed with software that directs the one or more processing units. Some of the software modules in the memory control the operation of the computing device with respect to generation, collection, and distribution or other use of data. In some cases, software directs the collection of individual datums, and in other cases, software directs the collection of sets of data.

Software may include a fully executable software program, a simple configuration data file, a link to additional directions, or any combination of known software types. When the computing server updates software, the update may be small or large. For example, in some cases, a computing server downloads a small configuration data file to as part of software, and in other cases, computing server completely replaces all of the present software on the computing device with a fresh version. In some cases, software, data, or software and data is encrypted, encoded, and/or otherwise compressed for reasons that include security, privacy, data transfer speed, data cost, or the like.

Processing devices, which may be identified herein as "processing units, "processors," or some other like term, as described herein, include central processing units (CPU's), microprocessors, microcontrollers (MCU), digital signal processors (DSP), application specific integrated circuits (ASIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. A processor may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

As known by one skilled in the art, a computing device, including a mobile computing device, has one or more memories, and each memory may comprise any combination of volatile and non-volatile computer-readable media for reading and writing. Volatile computer-readable media includes, for example, random access memory (RAM). Non-volatile computer-readable media includes, for example, any one or more of read only memory (ROM), magnetic media such as a hard-disk, an optical disk, a flash memory device, a CD-ROM, and the like. In some cases, a particular memory is separated virtually or physically into separate areas, such as a first memory, a second memory, a third memory, etc. In these cases, it is understood that the different divisions of memory may be in different devices or embodied in a single memory. Some or all of the stored contents of a memory may include software instructions executable by a processing device to carry out one or more particular acts.

The computing devices illustrated herein may further include operative software found in a conventional computing device such as an operating system or task loop, software drivers to direct operations through I/O circuitry, networking circuitry, and other peripheral component circuitry. In addition, the computing devices may include operative application software such as network software for communicating with other computing devices, database software for building and maintaining databases, and task management software where appropriate for distributing the communication and/or operational workload amongst various processors. In some cases, the computing device is a single hardware machine having at least some of the hardware and software listed herein, and in other cases, the computing device is a networked collection of hardware and software machines working together in a server farm to execute the functions of one or more embodiments described herein. Some aspects of the conventional hardware and software of the computing device are not shown in the figures for simplicity.

When so arranged as described herein, each computing device may be transformed from a generic and unspecific computing device to a combination device arranged comprising hardware and software configured for a specific and particular purpose such as to provide a determined technical solution. When so arranged as described herein, to the extent that any of the inventive concepts described herein are found by a body of competent adjudication to be subsumed in an abstract idea, the ordered combination of elements and limitations are expressly presented to provide a requisite inventive concept by transforming the abstract idea into a tangible and concrete practical application of that abstract idea.

The embodiments described herein use computerized technology to improve the technology of radiation-based disinfection, but there other techniques and tools remain available to disinfect medical devices and other objects. Therefore, the claimed subject matter does not foreclose the whole or even substantial radiation-based disinfection technological area. The innovation described herein uses both new and known building blocks combined in new and useful ways along with other structures and limitations to create something more than has heretofore been conventionally known. The embodiments improve on computing systems which, when un-programmed or differently programmed, cannot perform or provide the specific radiation-based disinfection system features claimed herein. The embodiments described in the present disclosure improve upon known radiation-based disinfection processes and techniques. The computerized acts described in the embodiments herein are not purely conventional and are not well understood. Instead, the acts are new to the industry. Furthermore, the combination of acts as described in conjunction with the present embodiments provides new information, motivation, and business results that are not already present when the acts are considered separately. There is no prevailing, accepted definition for what constitutes an abstract idea. To the extent the concepts discussed in the present disclosure may be considered abstract, the claims present significantly more tangible, practical, and concrete applications of said allegedly abstract concepts. And said claims also improve previously known computer-based systems that perform radiation-based disinfection operations.

In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the systems, methods, and apparatus described in the present disclosure.

FIGS. 9 to 12 are data flow diagrams illustrating processes that may be used by embodiments of computing devices such as disinfection systems 100. In this regard, each described process may represent a module, segment, or portion of code, which comprises one or more executable instructions for implementing the specified logical function(s). It should also be noted that in some implementations, the functions noted in the process may occur in a different order, may include additional functions, may occur concurrently, and/or may be omitted.

As used herein, the term "module" refers to an electronic circuit, a processor unit (e.g., shared, dedicated, group, single core, multicore, or the like) and memory operative to execute one or more software or firmware programs, an application specific integrated circuit (ASIC), a combinational logic circuit, or some other individual or cooperative coupling of suitable components (either hardware or software) that provides the functionally described with respect to the module.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis (e.g., measuring radiation with sensors, determining if a minimum dose of radiation has been delivered, and the like). An example of an activity that is not real-time is one that occurs over an extended period of time (e.g., hours or days) or that occurs based on intervention or direction by a person or other activity.

Where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a disinfection chamber may include a plurality of radiation sources mounted "substantially parallel." In these cases, a two radiation sources that are mounted exactly parallel are mounted along a common "X" axis and a "Y" axis that is normal (i.e., 90 degrees or at right angle) to a plane or line formed by a "Z" axis. Different from the exact precision of the term, "parallel," and the use of "substantially" or "about" to modify the characteristic permits a variance of the particular characteristic by up to 30 percent.

In the foregoing description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed as including "and/or" unless the context clearly dictates otherwise.

As used herein, the term "about" or "approximately" when used in conjunction with a number refers to any number within one percent, five percent, or ten percent (1%, 5% or 10%) of the referenced number.

The headings and Abstract of the Disclosure provided herein are for convenience only and do not interpret the scope or meaning of the embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a disinfection chamber having an interior volume;
a radiation source arranged to emit radiation into the interior volume of the disinfection chamber;
at least one radiation sensor circuit arranged to detect the radiation within the interior volume of the disinfection chamber;
an independent monitoring circuit arranged to detect the radiation within the interior volume of the disinfection chamber; and
a computing device that comprises:
a memory arranged to store:
first radiation values captured by the at least one radiation sensor circuit;
second radiation values captured by the independent monitoring circuit; and
computer instructions; and;

a processor arranged to execute the computer instructions which, when executed by the processor, cause the processor to:
  direct the radiation source to start emitting the radiation into the interior volume of the disinfection chamber;
  generate a first accumulated radiation value based on the first radiation values stored in the memory;
  generate a second accumulated radiation value based on the second radiation values stored in the memory;
  direct the radiation source to stop emitting the radiation into the interior volume of the disinfection chamber after the first accumulated radiation value has reached a first radiation threshold;
  determine a validation result based on a comparison of the first accumulated radiation value to the second accumulated radiation value; and
  assert, based on the validation result, a validated disinfection signal or an error signal;
wherein the processor is also arranged to monitor a disinfection cycle; and
wherein the system determines, based on the validation result, whether to validate or invalidate the disinfection cycle.

2. The system of claim 1, further comprising:
a first photodiode arranged in the at least one radiation sensor circuit;
a second photodiode in the at least one radiation sensor circuit; and
a third photodiode in the independent monitoring circuit.

3. The system of claim 2, wherein the processor is arranged to execute the computer instructions which, when executed by the processor, cause the processor further to:
  generate the first accumulated radiation value from a mathematical combination of first radiation information captured by at least the first and second photodiodes; and
  generate the second accumulated radiation value from second radiation information captured by the third photodiode.

4. The system of claim 3, wherein the processor is arranged to execute the computer instructions which, when executed by the processor, cause the processor further to:
  apply at least one first calibration factor during the generation of the first accumulated radiation value; and
  apply at least one second calibration factor during the generation of the second accumulated radiation value.

5. The system of claim 2, wherein the processor includes at least two different processors, the at least two different processors including a first processor arranged to receive first radiation information from the at least one radiation sensor circuit and a second processor arranged to receive second radiation information from the independent monitoring circuit.

6. The system of claim 5, wherein the first processor is arranged to not receive second radiation information from the independent monitoring circuit and the second processor is arranged to not receive second radiation information from the at least one radiation sensor circuit.

7. The system of claim 1, further comprising:
a first photodiode arranged in the at least one radiation sensor circuit the first photodiode positioned at a first location in the interior volume of the disinfection chamber;
a second photodiode arranged in the at least one radiation sensor circuit the second photodiode positioned at a second location in the interior volume of the disinfection chamber; and
a third photodiode arranged in the independent monitoring circuit, the third photodiode positioned at a third location in the interior volume of the disinfection chamber, wherein the first location, the second location, and the third location are different locations.

8. The system of claim 7, wherein the second location and the third location are in close proximity to each other.

9. The system of claim 1, wherein the processor is communicatively coupled to both the at least one radiation sensor circuit and the independent monitoring circuit.

10. The system of claim 9, further comprising a second processor communicatively coupled to only one of the at least one radiation sensor circuit and the independent monitoring circuit.

11. The system of claim 1, further comprising a power supply circuit electrically coupled to only one of the at least one radiation sensor circuit and the independent monitoring circuit.

12. A system, comprising:
a disinfection chamber having an interior volume;
a radiation source arranged to emit radiation into the interior volume of the disinfection chamber;
at least one radiation sensor circuit arranged to detect the radiation within the interior volume of the disinfection chamber;
an independent monitoring circuit arranged to detect the radiation within the interior volume of the disinfection chamber; and
a computing device that comprises:
  a memory arranged to store:
    first radiation values captured by the at least one radiation sensor circuit;
    second radiation values captured by the independent monitoring circuit; and
    computer instructions; and;
  a processor arranged to execute the computer instructions which, when executed by the processor, cause the processor to:
    direct the radiation source to start emitting the radiation into the interior volume of the disinfection chamber;
    generate a first accumulated radiation value based on the first radiation values stored in the memory;
    generate a second accumulated radiation value based on the second radiation values stored in the memory;
    direct the radiation source to stop emitting the radiation into the interior volume of the disinfection chamber after the first accumulated radiation value has reached a first radiation threshold;
    determine a validation result based on a comparison of the first accumulated radiation value to the second accumulated radiation value; and
    assert, based on the validation result, a validated disinfection signal or an error signal;
wherein the processor is also arranged to monitor a disinfection cycle;
wherein the system determines, based on the validation result, whether to validate or invalidate the disinfection cycle; and
wherein the processor includes at least two different processors, the at least two different processors including a first processor arranged to receive first radiation information from the at least one radiation sensor circuit and a second processor arranged to receive second radiation information from the independent monitoring circuit; and wherein the first processor is arranged to not receive second radiation information from the independent monitoring circuit and the second processor is arranged to not receive second radiation information from the at least one radiation sensor circuit.

13. A system, comprising:

a disinfection chamber having an interior volume;

a radiation source arranged to emit radiation into the interior volume of the disinfection chamber;

at least one radiation sensor circuit arranged to detect the radiation within the interior volume of the disinfection chamber;

an independent monitoring circuit arranged to detect the radiation within the interior volume of the disinfection chamber; and a computing device that comprises:
  a memory arranged to store:
    first radiation values captured by the at least one radiation sensor circuit;
    second radiation values captured by the independent monitoring circuit; and
    computer instructions; and;
  a processor arranged to execute the computer instructions which, when executed by the processor, cause the processor to:
    direct the radiation source to start emitting the radiation into the interior volume of the disinfection chamber;
    generate a first accumulated radiation value based on the first radiation values stored in the memory;
    generate a second accumulated radiation value based on the second radiation values stored in the memory;
    direct the radiation source to stop emitting the radiation into the interior volume of the disinfection chamber after the first accumulated radiation value has reached a first radiation threshold;
    determine a validation result based on a comparison of the first accumulated radiation value to the second accumulated radiation value; and
    assert, based on the validation result, a validated disinfection signal or an error signal;

wherein the processor is also configured to monitor a disinfection cycle;

wherein the system determines, based on the validation result, whether to validate or invalidate the disinfection cycle; and wherein the system further comprises:

a first photodiode arranged in the at least one radiation sensor circuit the first photodiode positioned at a first location in the interior volume of the disinfection chamber;

a second photodiode arranged in the at least one radiation sensor circuit the second photodiode positioned at a second location in the interior volume of the disinfection chamber; and a third photodiode arranged in the independent monitoring circuit, the third photodiode positioned at a third location in the interior volume of the disinfection chamber, wherein the first location, the second location, and the third location are different locations.

* * * * *